United States Patent
Woodbury et al.

(10) Patent No.: US 9,970,932 B2
(45) Date of Patent: May 15, 2018

(54) NON-COVALENT PATTERNED CHEMICAL FEATURES AND USE THEREOF IN MALDI-BASED QUALITY CONTROL

(71) Applicant: ARIZONA BOARD OF REGENTS ON BEHALF OF ARIZONA STATE UNIVERSITY, Scottsdale, AZ (US)

(72) Inventors: Neal Woodbury, Tempe, AZ (US); Stephen Johnston, Tempe, AZ (US); Zhan Gong Zhao, Tuscon, AZ (US); Matthew Greving, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days. days.

(21) Appl. No.: 14/773,751

(22) PCT Filed: Mar. 14, 2014

(86) PCT No.: PCT/US2014/028771
§ 371 (c)(1),
(2) Date: Sep. 8, 2015

(87) PCT Pub. No.: WO2014/144383
PCT Pub. Date: Sep. 18, 2014

(65) Prior Publication Data
US 2016/0041158 A1    Feb. 11, 2016

Related U.S. Application Data

(60) Provisional application No. 61/799,469, filed on Mar. 15, 2013.

(51) Int. Cl.
*G01N 33/543* (2006.01)
*G01N 27/62* (2006.01)
*G01N 33/53* (2006.01)
*G01N 33/68* (2006.01)
*C12Q 1/68* (2018.01)

(52) U.S. Cl.
CPC .............................. *G01N 33/54366* (2013.01)

(58) Field of Classification Search
CPC ............................................... G01N 33/54366
USPC .......................................... 506/9, 12, 16, 18
See application file for complete search history.

(56) References Cited

U.S. PATENT DOCUMENTS

| | | |
|---|---|---|
| 5,143,854 A | 9/1992 | Pirrung et al. |
| 5,571,639 A | 11/1996 | Hubbell et al. |
| 5,593,839 A | 1/1997 | Hubbell et al. |
| 6,620,584 B1 | 9/2003 | Chee et al. |
| 7,569,343 B2 | 8/2009 | Marton et al. |
| 2004/0265923 A1 | 12/2004 | Gilmore et al. |
| 2005/0037398 A1* | 2/2005 | Gelfand ............... C12Q 1/6869 435/6.11 |
| 2005/0186580 A1* | 8/2005 | Dellinger ............ B01J 19/0046 435/6.11 |
| 2006/0160234 A1 | 7/2006 | Lopez-Avila et al. |
| 2006/0166199 A1 | 7/2006 | Marton et al. |
| 2006/0282221 A1 | 12/2006 | Shah et al. |
| 2008/0157786 A1 | 7/2008 | Holt et al. |
| 2012/0029056 A1 | 2/2012 | Alevizos et al. |
| 2014/0080721 A1* | 3/2014 | Klausing ................ C40B 20/04 506/4 |

FOREIGN PATENT DOCUMENTS

| | | |
|---|---|---|
| EP | 0476014 A1 | 3/1992 |
| EP | 0624059 A1 | 11/1994 |
| EP | 0728520 A1 | 8/1996 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-03029459 A2 | 4/2003 |
| WO | WO-2004003233 A1 | 1/2004 |
| WO | WO-2007018656 A2 | 2/2007 |
| WO | WO-2008048970 A2 | 4/2008 |
| WO | WO-2009140039 A2 | 11/2009 |

OTHER PUBLICATIONS

Greving et al. (Langmuir 2010, 26(3), 1456-1459; see IDS).*
Fulong et al. Bioorganic & Medicinal Chemistry 10 (2002) 3637-3647.*
Breitling F. et al. High-density peptide arrays. Mol. BioSyst., vol. 5, pp. 224-234, 2009.
Cretich, M. et al. Protein and peptide arrays: recent trends and new directions. Biomol Eng. vol. 23, No. 2-3, pp. 77-88, Jun. 2006.
Fodor. Multiplexed biochemical assays with biological chips. (1993) Nature 364: 555-556.
Greving et al., Feature-level MALDI-MS characterization of in situ-synthesized peptide microarrays, Langmuir, Feb. 2009, 1456-1459, vol. 26, No. 3.
International Application No. PCT/US2014/028771 International Preliminary Report on Patentability and Written Opinion dated Sep. 24, 2015.
International Application No. PCT/US2014/028771 International Search Report and Written Opinion dated Jul. 17, 2014.
International Application No. PCT/US2014/029822 International Preliminary Report on Patentability and Written Opinion dated Sep. 15, 2015.
International Application No. PCT/US2014/029822 International Search Report and Written Opinion dated Sep. 2, 2014.
Min et al. Peptide arrays: towards routine implementation. Current Opinion in Chemical Biology vol. 8, pp. 554-558, 2004.
Stafford P, and Johnston, Microarray technology displays the complexities of the humoral immune response. Expert Rev. Mol. Diagn. vol. 11, No. 1, pp. 5-8, Jan. 2011.
U.S. Appl. No. 14/773,750 Office Action dated Aug. 10, 2016.
U.S. Appl. No. 14/773,750 Final Office Action dated Apr. 27, 2017.
U.S. Appl. No. 14/773,750 Advisory Office Action dated Aug. 10, 2017.

* cited by examiner

*Primary Examiner* — Janet L Epps-Smith
(74) *Attorney, Agent, or Firm* — Wilson Sonsini Goodrich & Rosati

(57) ABSTRACT

The present application provides arrays for use in immunosignaturing and quality control of such arrays. Also disclosed are peptide arrays and uses thereof for diagnostics, therapeutics and research.

23 Claims, 19 Drawing Sheets

Proper Synthesis

Coupling Failure in Cycle 5: Substitution

Figure 8, examples of safety catch linkers; activation and cleavage. R = peptides and other chemical entities.

Figure 9. Example of chemical labelling for enhancing MALDI sensitivity. R = peptides and other chemical entities.

NON-COVALENT PATTERNED CHEMICAL FEATURES AND USE THEREOF IN MALDI-BASED QUALITY CONTROL

CROSS-REFERENCE

This application is a U.S. National Stage Application of PCT/US2014/028771, filed on Mar. 14, 2013, which claims the benefit of U.S. Provisional Application No. 61/799,469, filed on Mar. 15, 2013, which is incorporated by reference herein in its entirety.

STATEMENT AS TO FEDERALLY SPONSORED RESEARCH

This invention was made with government support under Grant. No. HDTRA1-11-1-0010 and Contract No. HDTRA1-12-C-0058 awarded by the Defense Threat Reduction Agency and Grant No. MCB-1243082 awarded by the National Science Foundation. The government has certain rights in the invention.

BACKGROUND OF THE INVENTION

Screening mechanisms may be used for assessing samples for changes in polynucleotide and/or polypeptide concentration and/or expression. While there are some peptide arrays available commercially, such arrays have low density and relatively low fidelity.

SUMMARY OF THE INVENTION

There is a need for efficient, reproducible and low cost quality control techniques to assess the quality and reliability of microchip arrays during manufacturing and processing. The methods and processes provided herein enable the rapid screening and assessment of microchip arrays, specifically the fidelity and accuracy of target sequences on the array.

Accordingly, disclosed herein are methods, components and compositions for determining the quality of a biopolymer array of interest. The methods, components and compositions disclosed herein can be used to assess or determine if a biopolymer array has sufficient fidelity, accuracy, density and/or other characteristics necessary for performing diagnostic assays on the biopolymer arrays. The disclosed embodiments can be used as a primary quality control method, or can be used in conjunction with other quality control methods for assessing the quality of a biopolymer array of interest.

In one aspect, the methods, components and compositions are useful for determining the quality of a biopolymer array of interest. The biopolymer array may comprise a plurality of compounds coupled to the surface of the array, wherein the compounds are synthesized in situ. In some embodiments, the methods can be used to determine the quality of a biopolymer array prior to initiating a diagnostic procedure on the array. In other embodiments, the methods can be used to determine the quality of a biopolymer array concurrently with a diagnostic procedure, for example, for assessing the immunosignature of a subject or patient. In some embodiments, the subject is a mammal, avian or reptile. In other embodiments, the subject is human. In still other embodiments, the subject is a livestock animal, e.g., bovine, porcine or ovine species, dog, cat, bird, or other domestic or wild animal.

Provided herein are arrays of compounds or biopolymers, wherein a defined area of the array is designated for quality control analysis of the array. In some embodiments, the defined area of the array may comprise unique compound on separate features of the array. In other embodiments, the unique compounds on the array are capable of being released from the surface of the array without diffusion of the compounds outside of a boundary of the feature.

In some embodiments, the compounds on the array are not covalently bound to the surface of the array. In other embodiments, the compounds on the array are covalently bound to the surface of the array, but are capable of being released from the surface of the array.

In some embodiments, the array comprises a monolayer of greater than about 100 compounds per $cm^2$. In other embodiments, the array comprises a monolayer of greater than about 1,000 compounds per $cm^2$. In yet other embodiments, the array comprises a monolayer of greater than about 5,000 compounds per $cm^2$.

In some embodiments, the compounds of the array are bound to the surface of the array via a linker. In yet other embodiments, the linker is cleavable between the molecule and the surface of the array. In still other embodiments, the linker is acid labile, base labile or light labile. In yet other embodiments, the linker comprises a compound selected from the group of hydroxymethylbenzoic acid (HMBA), hydroxymethylphenylacetic acid (HMPAA), hydroxymethylphenoxyacetic acid (HMPOA), 4-(4-hydroxymethyl-3-methoxyphenoxyl)-butyric acid (HMPB), carboxyproanesulfonamide (CPSA), sulfamoylbenzoic acid (SABA) (and other safety-catch linkers), p-{(R,S)-a-[1-(9H-Fluoren-9-yl)-methoxyformamido]-2,4-dimethoxybenzyl}-phenoxyacetic acid, and variants thereof.

In one embodiment, the compounds to be measured on the array are coupled to a permanently ionized group. In still other embodiments, the compound is triphenylphosphine (TPP) or tris(2,4,6-trimethoxyphenyl)phosphine (TMPP). In yet other embodiments, the unique compounds are released under a volatile, nebulized or sublimated gas phase, or under a liquid phase wherein droplets of the liquid have a diameter comparable to the array feature size and pitch. In some embodiments, the compounds are peptides or nucleic acids.

Also disclosed herein are methods for evaluating the quality of an array, the method comprising: 1) assigning quality control features on the surface of the array; 2) generating unique compounds on each control feature; 3) releasing the compounds from the surface of the array without diffusion of the compounds outside of a boundary of the feature; and 4) analyzing the compounds for sequence fidelity using matrix assisted laser desorption/ionization-time of flight analysis.

In some embodiments, the array comprises a monolayer of greater than about 100 compounds per $cm^2$. In still other embodiments, the array comprises a monolayer of greater than about 1,000 compounds per $cm^2$. In yet other embodiments, the array comprises a monolayer of greater than about 5,000 compounds per $cm^2$.

In some embodiments, the compounds are not covalently bound to the surface upon generation on the array. In still other embodiments, the compounds are covalently bound to the surface upon generation on the array, but are capable of being cleaved from the surface of the array.

In one embodiment, the compounds are initially bound to the surface of the array via a linker. In some embodiments, the linker is cleavable between the molecule and the surface of the array. In other embodiments, the linker is acid labile, base labile or light labile. In still other embodiments, the linker comprises a compound selected from the group of hydroxymethylbenzoic acid (HMBA), hydroxymethylphenylacetic acid (HMPAA), hydroxymethylphenoxyacetic acid (HMPOA), 4-(4-hydroxymethyl-3-methoxyphenoxyl)-butyric acid (HMPB), carboxyproanesulfonamide (CPSA), sulfamoylbenzoic acid (SABA) (and other safety-catch linkers), p-{(R,S)-a-[1-(9H-Fluoren-9-yl)-methoxyformamido]-2,4-dimethoxybenzyl}-phenoxyacetic acid, and variants thereof.

In some embodiments, the compounds to be measured are coupled to a permanently ionized group. In still other embodiments, the compound is triphenylphosphine (TPP) or tris(2,4,6-trimethoxyphenyl)phosphine (TMPP). In yet other embodiments, the unique compounds are released under a volatile, nebulized or sublimated gas phase, or under a liquid phase wherein droplets of the liquid have a diameter comparable to the array feature size and pitch. In still other embodiments, the compounds are peptides or nucleic acids.

Also disclosed herein are methods for evaluating the quality of an array, and determining the type of error during synthesis of the peptides onto the array, the method comprising a. assigning quality control features on the surface of the array, wherein each feature contains a linker peptide for each synthesis step to be performed; b. initiating photolithography on one of the features of step (a) containing a linker peptide; c. initiating an amino acid coupling reaction to the linker peptide on the feature; and d. determining the identity of the amino acid coupled, if any, to the linker peptide; wherein if the linker peptide in step (c) was not deprotected, no amino acid would be coupled to the linker peptide and the event would be registered as a deletion of an amino acid, and wherein if the amino acid in step (c) failed to couple to the linker peptide, a substitution event would be registered.

INCORPORATION BY REFERENCE

All publications (including GenBank Accession numbers and the like), patents, and patent applications mentioned in this specification are herein incorporated by reference to the same extent as if each individual publication, patent, or patent application was specifically and individually indicated to be incorporated by reference. If more than one version of a sequence is associated with a deposit number at different times, the version associated with the deposit number at the effective time of filing the application is meant.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
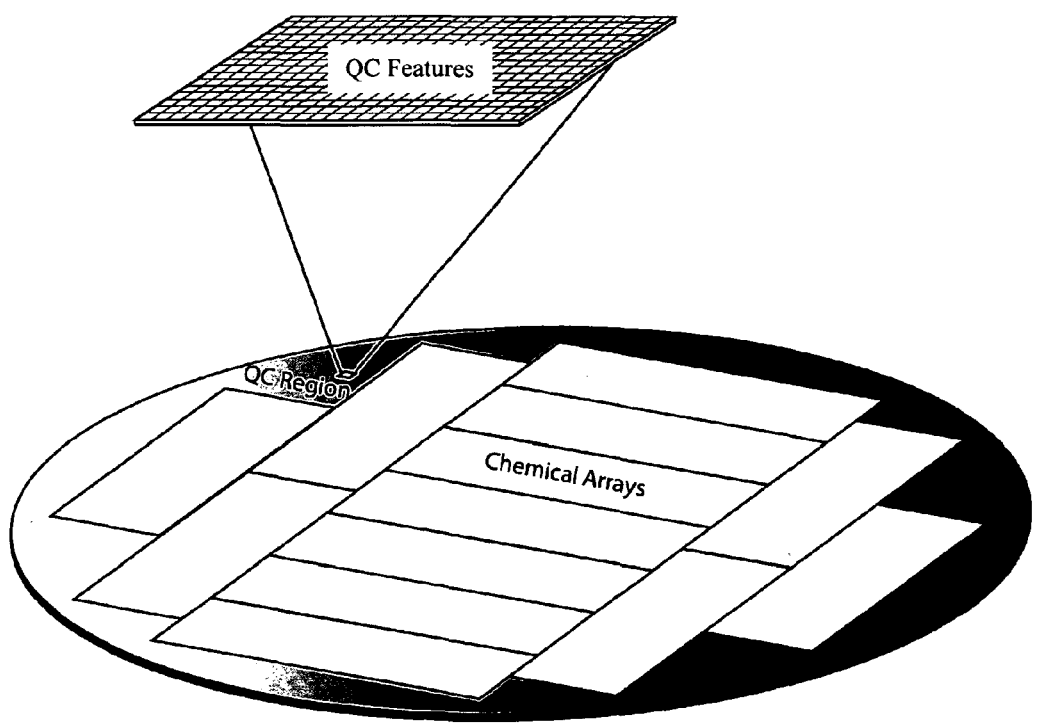
FIG. 1 illustrates that QC features can be placed in parts of the wafer not used for chemical arrays: one representative arrangement is shown.

Specific binding refers to the binding of a compound to a target (e.g., a component of a sample) that is detectably higher in magnitude and distinguishable from non-specific binding occurring to at least one unrelated target. Specific binding can be the result of multiple, structurally specific interactions between particular chemical groups in the ligand and its binding partner or a particular spatial fit (e.g., lock and key type) whereas nonspecific binding is usually the result of interactions in which there is not particular spatial arrangement of the ligand relative to its binding partner (e.g., general hydrophobic or charge-charge interactions that do not result in a specific structure of the binding pair). Specific binding does not however imply that a compound binds one and only one target. Thus, a compound can and often does show specific binding of different strengths to several different targets and only nonspecific binding to other targets. Preferably, different degrees of specific binding can be distinguished from one another as can specific binding from nonspecific binding. Specific binding often involves an apparent association constant of $10^3$ or higher, where the concentrations of components in the unit-less association constant are defined relative to their standard states (this is true for all association constant values listed in this specification).

An association constant is an equilibrium constant for the binding reaction between a ligand (L) and its binding partner (B):

$$L + B \leftarrow \rightarrow LB, K_{assoc} = \frac{\left(\frac{LB}{LB_0}\right)}{\left(\frac{L}{L_0} \times \frac{B}{B_0}\right)}$$

where L, B and LB in this equation are the concentrations of the ligand, binding partner and the ligand/binding partner complex, respectively, and $L_0$, $B_0$ and $LB_0$ are the standard state concentrations of ligand, binding partner and the ligand/binding partner complex, respectively. The dissociation constant for the same binding interaction would be given by $1/K_{assoc}$. The term "apparent association constant" refers to the value calculated for $K_{assoc}$ as defined above under conditions where one or more binding partner molecules are confined spatially, such as on a surface, such that multiple binding partners are in close enough proximity to act in concert or the confined environment, such as a surface alters the nature of the interaction between the ligand and the binding partner. The term "apparent dissociation constant" refers to the inverse of the apparent association constant. In the text contained in this document, the use of the terms "association constant" or "dissociation constant" may include both true and apparent association and dissociation constants.

Specific binding can additionally or alternatively be defined as a binding strength (e.g., fluorescence intensity) more than three standard deviations greater than background represented by the mean binding strength of empty control areas in an array (i.e., having no compound, where any binding is nonspecific binding to the support). The range of affinities or avidities of compounds showing specific binding to a monoclonal or other sample can vary by from about 1 to about 4 and often from about 2.5 to about 3.5 orders of magnitude. An apparent association constant includes avidity effects if present (in other words, if a target shows enhanced affinity to multiple molecules of the same compound, the apparent association constant is a value reflecting the aggregate binding of the multiple molecules of the same compound to the target). When contacted with a random selection of monoclonal antibodies, a subset of compounds (e.g., from about 1 to about 20, or from about 5 to about 15%) have association constants in the range of from about $10^3$ to about $10^6$, from about $2\times10^3$ to about $10^6$ or from about $10^4$ to about $10^6$ to at least one and sometimes several (e.g., at least about 2, about 5 or about 10) different targets. A subset of all peptides or other compounds (e.g., at least about 1%, at least about 5% or about 10%; from about 1 to about 75%, from about 5 to about 60%, from about 1 to about 20% or from about 5 to about 15%) usually shows actual association constants of from about $10^3$ to about $10^6$ to at least one and usually several targets (e.g., at least about 2, about 5 or about 10). The same ranges of association constant apply to composite targets binding to the same compound in a complex sample. Of course different compounds in an array have different degrees of binding strength to components of a sample and some compounds can bind with higher or lower apparent association constants than these ranges.

Avidity is defined as enhanced binding of a component in solution to a surface that includes multiple copies of a compound, such as a peptide, that the solution component has affinity for. In other words, given a compound on a surface that individually has some affinity for a component of a solution, avidity reflects the enhanced apparent affinity that arises when multiple copies of the compound are present on the surface in close proximity. Avidity is distinct from cooperative binding in that the interaction does not involve simultaneous binding of a particular molecule from the solution to multiple molecules of the compound on the surface. Avidity interactions and/or cooperative binding can occur during the association of components of a solution, such as antibodies in blood, with compounds on a surface.

Patients include humans, veterinary animals, such as cats, dogs, horses, farm animals, such as chickens, pigs, sheep, cattle and laboratory animals, such as rodents, e.g., mice and rats.

A binding profile of an array is a measure of the amount of component(s) of a sample bound to the different compounds of an array to a particular sample. The amount of component(s) bound reflects the amount of the components in the sample as well as the binding strength of components to the compounds. A binding profile can be represented for example as a matrix of binding strengths corresponding to the different compounds in an array. A binding profile typically includes binding strengths of a plurality of compounds (e.g., at least 2, 10, 50, 100 or 1000 having dissociation constants in a range of from about $10^{-3}$ to about $10^{-6}$ to a sample.

Binding strength can be measured by association constant, dissociation constant, dissociation rate, or association rate, or a composite measure of affinity which may include one or more of these measures. The strength of a signal from a labeled component of a sample bound to immobilized compounds can provide a value for general affinity. If a term used to define binding strength is referred to as "apparent" what is meant is a measured value without regard to multivalent binding. For example, the measured value of an association constant under conditions of multivalent binding includes a plurality of effects due to monovalent binding, among other factors. Unless otherwise specified, binding strength can refer to any of these measures referred to above.

The term "nucleic acids" includes any and all forms of alternative nucleic acid containing modified bases, sugars, and backbones including peptide nucleic acids and aptamers, optionally, with stem loop structures.

The term "polypeptide" is used interchangeably with "peptide" and in its broadest sense to refer to a sequence of subunit natural amino acids, amino acid analogs including unnatural amino acids. Peptides include polymers of amino acids having the formula $H_2NCHRCOOH$ (α-amino acids), the formula $H_2NCHRCHRCOOH$ (β-amino acids) and/or analog amino acids having the formula $HRNCH_2COOH$. The subunits are linked by peptide bonds (i.e., amide bonds), except as noted. Often all subunits are connected by peptide bonds. The polypeptides may be naturally occurring, processed forms of naturally occurring polypeptides (such as by enzymatic digestion), chemically synthesized or recombinantly expressed. Preferably, the polypeptides are chemically synthesized using standard techniques. The polypeptides may comprise D-amino acids (which are resistant to L-amino acid-specific proteases), a combination of D- and L-amino acids, beta amino acids, and various other "designer" amino acids (e.g., beta-methyl amino acids, Ca-methyl amino acids, and Na-methyl amino acids) to convey special properties. Synthetic amino acids include ornithine for lysine, and norleucine for leucine or isoleucine. Hundreds of different amino acid analogs are commercially available from e.g., PepTech Corp., MA. In general, unnatural amino acids have the same basic chemical structure as a naturally occurring amino acid, i.e., an a carbon that is bound to a hydrogen, a carboxyl group, an amino group, and an R group.

In addition, polypeptides can have non-peptide bonds, such as N-methylated bonds (—N(CH$_3$)—CO—), ester bonds (—C(R)H—C—O—O—C(R)—N—), ketomethylen bonds (—CO—CH$_2$—), aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH═CH—), retro amide bonds (—NH—CO—), peptide derivatives (—N(R)—CH$_2$—CO—), wherein R is the "normal" side chain. These modifications can occur at any of the bonds along the peptide chain and even at several (2-3) at the same time. For example, a peptide can include an ester bond. A polypeptide can also incorporate a reduced peptide bond, i.e., $R_1$—CH$_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The compounds can also be peptoids (N-substituted glycines), in which the sidechains are appended to nitrogen atoms along the molecule's backbone, rather than to the α-carbons, as in amino acids.

The term "polysaccharide" means any polymer (homopolymer or heteropolymer) made of subunit monosaccharides, oligimers or modified monosaccharides. The linkages between sugars can include acetal linkages (glycosidic bonds), ester linkages (including phophodiester linkages), amide linkages, and ether linkages.

General

The invention provides arrays of compounds, and methods of analyzing the arrays, for use in profiling samples. The arrays include compounds binding to components of the samples at relatively low affinities. Although practice of the invention is not dependent on an understanding of mechanism, it is believed that under conditions of monovalent binding, different degrees of specific binding might be difficult to distinguish from each other and from nonspecific binding. However, the affinity of compounds binding to components of the samples can be increased by forming arrays such that components of the samples (e.g., antibodies or cells) can bind to more than one molecule of a compound at the same time or through avidity interactions with high densities of the compounds on the surface. When a sample is applied to an array under such conditions, the compounds of the array bind to component(s) of the sample with significantly different affinities generating a profile characteristic of the sample. Such a profile usually includes some compounds having no specific binding to components of the sample and other compounds having different degrees of specific binding to components of the sample. Although such binding interactions are specific in the sense that overall binding profiles of an array are reproducible for replicates of the same sample and distinguishable between different samples, they are not necessarily unique in that compounds in the array usually show specific binding albeit of different degrees to a number of different components of a sample or different samples.

The affinity or apparent affinity of informative compounds (i.e., those showing distinguishable binding to different targets) in an array can be measured for monoclonal antibody samples. When measured against monoclonal antibodies that do not bind to a selected target, informative compounds in some arrays often show apparent affinity association constants in a range of from about $10^4$ to about $10^9$, from about $10^6$ to about $10^9$, from about $10^4$ to about $10^7$, or from about $10^4$ to about $10^6$. Association constants of such informative compounds are often within a range of from about $10^3$ to about $10^6$, or from about $10^4$ to about $10^5$. When measured against a complex sample, similar ranges of apparent or actual association constants are observed; however, in this case, the constants are a composite of values for multiple different components within a sample binding to the same compound. Such affinities can be distinguished from nonspecific interactions. The proportion of informative compounds (i.e., compounds that show distinguishable binding among different targets) can vary depending on the composition of the array and the sample, but ranges of from about 0.1 to about 50%, from about 1 to about 30%, from about 0.1 to about 20%, from about 1 to about 15%, or from about 3 to about 12% provide some guide. Given that monoclonal antibodies each have their own signature consisting of binding to many compounds on the surface, it might have seemed impossible to meaningfully resolve patient serum samples which may contain $10^8$ or more distinct antibodies with different binding specificities. When an array is hybridized against a complex sample, such as from a patient or subject, the binding profile represents the aggregate effect of multiple components of a sample. Surprisingly despite the complexity of the samples, different samples are associated with different binding profiles. Also surprisingly, the intensity of binding profile often differs between patients with a disease or at risk of disease relative to normal patients.

The binding profile of such an array to a sample can be used to characterize a sample. For example, the binding profile can be compared with binding profiles known to be associated with different diseases or stages of diseases or lack of diseases. Alternatively or additionally, the binding can be analyzed, for example, by using a compound binding relatively strongly to a component of the sample to affinity purify an antibody from the sample, or by comparing the sequence of a peptide in the array known to bind strongly to a component of a sample with a protein database to identify a protein in the sample. Remarkably, the same array can generate different and informative profiles with many different samples representing different disease states, disease stages, lack of disease and the like. Moreover, a profile characteristic of disease or departure from a non-disease state can be detected very early in development of a disease before typical analytical markers of disease would be detectable by conventional methods, such as ELISA.

Non-Covalent Patterned Chemical Features and Use in MALDI-Based QC.

The methods and compositions disclosed herein are directed in part to the creation of relatively large chemical libraries through in situ synthesis on solid surfaces forming patterns of synthetic molecules on these surfaces. Two types of chemical libraries currently made and sold commercially in this way include arrays of oligonucleotide libraries and peptide libraries. Commercial vendors of such in situ synthesized libraries include Nimblegen-Roche, Affymetrix, PEPperPRINT, Agilent, and LC Sciences.

Other types of chemical libraries included herein may use similar methods, including peptoid libraries, peptide nucleic acid (PNA) libraries and other patterned chemical libraries on surfaces. The libraries do not have to be restricted to phosphodiester or amide bonds. Ester bonds, thioester bonds, ether bonds, carbon-carbon bonds are examples of other bonds that could be formed and many types of chemistry can be used to create these bonds, as has been demonstrated in general for solid phase synthesis and is well known to those in the art.

The libraries synthesized in these ways are not be restricted to linear structures. Also included in the methods and compositions described herein are branched structures. Branched and branched-type structures have been demonstrated with the methods disclosed herein, and it is possible to add groups to an existing molecular scaffold as well. The monomer molecules used to make these in situ synthesized patterned chemical arrays do not have to be natural amino acids or nucleic acids, but could include a broad range of chemical types.

It is even possible to make patterned chemicals on surfaces using monomer molecules of different types and with different bonding connections. Patterning can be done using any of a large number of methods including photolithography acting on photolabile groups or photolithography acting on molecules that produce acid or base, or the use of electrodes to oxidize or reduce compounds or direct printing of chemicals onto surfaces containing the reactive compounds, or any of a number of other means of patterning compounds on a surface in such a way that they react to form new molecular species.

One issue faced by all manufacturers of patterned chemical surfaces is the need for quality control analysis methods. The methods currently in use depend on the types of arrays. For DNA arrays, the typical approach is specific hybridization due to the high level of specificity and discrimination that provides for DNA sequences. For peptide arrays, the only measurement of library quality/composition on the surface currently in use is indirect, which is to bind monoclonal antibodies to specific peptide sequences.

The difficulty with these types of molecular recognition approaches is that, while they do report on presence or absence of a particular sequence, they do not give an indication of what contaminating compounds may also be present or whether the sequence other than the correct sequence/epitope itself is present.

Recently, Matrix Assisted Laser Desorption Ionization-Time of Flight (MALDI-TOF) mass spectrometry has developed to a point where it is possible to perform relatively high resolution imaging of surfaces and obtain mass spectra of monolayer features only tens of microns in size at high-throughput readout rates (more than 1 sample/second). MALDI-TOF is an analytical method based on laser ionization of the analyte molecules (e.g. oligonucleotides or peptides) with the matrix assistance, subsequent measurement of the fly-through time of ionized molecules through a fly tube, and determining of the corresponding molecular mass.

MALDI-TOF systems provided low per-feature analysis cost compared to liquid-chromatography mass spectrometry. In addition, when compared to a single optical signal obtained when binding a labeled monoclonal antibody, MALDI mass spectrometry is information rich allowing one to detect hundreds of signals in a single readout thereby providing a measure of the chemical composition of an array feature. Since MALDI mass spectrometry is a direct chemical measure, in contrast to an indirect measure of an antibody binding event, MALDI mass spectrometry is less prone to non-specific background that complicates interpretation of the QC data.

To utilize this direct chemical analysis approach for QC of in situ patterned chemical synthesis requires several items: (1) generation of QC features on the surfaces in physical positions and of physical sizes such that they can be assayed by this method; (2) a process for performing a series of chemical patterning steps at these positions that generates the maximum information about the process for which QC is desired; (3) a method for enhancing to the extent possible the signal from monolayers on a surface; and (4) a method for releasing the synthesized molecules from the surface without diffusion on the scale of the feature size.

The present inventors have identified new means by which MALDI may be used to improve quality control of peptide array analysis. MALDI-TOF analysis allows a sensitive, specific and low-cost means for routine quality control analysis of large synthetic peptide arrays.

Generation of QC Features to be Assayed.

Fifty (50) to 1000 micron features are optimal sizes for MALDI-TOF imaging using modern spectrophotometers (e.g. as can be purchased from Bruker). Because of the kinds of processing described below, one would normally put these features in a region of the surface where they can be physically separated (e.g., via dicing) from the remainder of the surface, as shown in FIG. 1. In this nonbinding example, QC features are placed in array format in a region of the wafer that does not overlap with the portions of the wafer that are provided to the customer.

Another option is to place QC features directly on the region of the wafer provided to the customer and to select a fraction of the production products for chemical analysis and/or to use such features to evaluate returned materials from the customer.

Stepwise Analysis of Processes.

An important aspect of the QC in a process that involves large numbers of fabrication cycles is to be able to determine exactly which cycle(s) in a process has failed or underperformed and what part of that cycle was faulty. A cycle is the repetitive set of procedures for patterned removal of a blocking group from the growing chain or structure of monomers followed by addition of a new monomer to the growing chain. The removal of the blocking group will be referred to as deprotection and the addition of a new monomer will be referred to as coupling. A nonbinding example would be the fabrication of a set of 10 amino acid long peptides on a surface. This might entail running one fabrication cycle for each possible amino acid (20 natural amino acids) ten times (one set of 20 steps for each amino acid residue in the peptide). The total number of process cycles would be 200. Each cycle would consist of a deprotection step and a coupling step. It is necessary to be able to individually evaluate each cycle and within a cycle the deprotection and coupling steps.

If deprotection fails, no monomer can be attached in the coupling step. This results in a deletion of that monomer from the growing chain. If the coupling event fails then the next monomer coupled will take its place (likely a different monomer) and thus a substitution will occur. Performing a chemical QC using MALDI mass spectrometry can detect these kinds of chemical synthesis events accurately. One way to do this is to include enough full length peptides in the QC region so that all steps are included. This has the value that it also allows the evaluation of each step in multiple sequence contexts.

Figure 2:
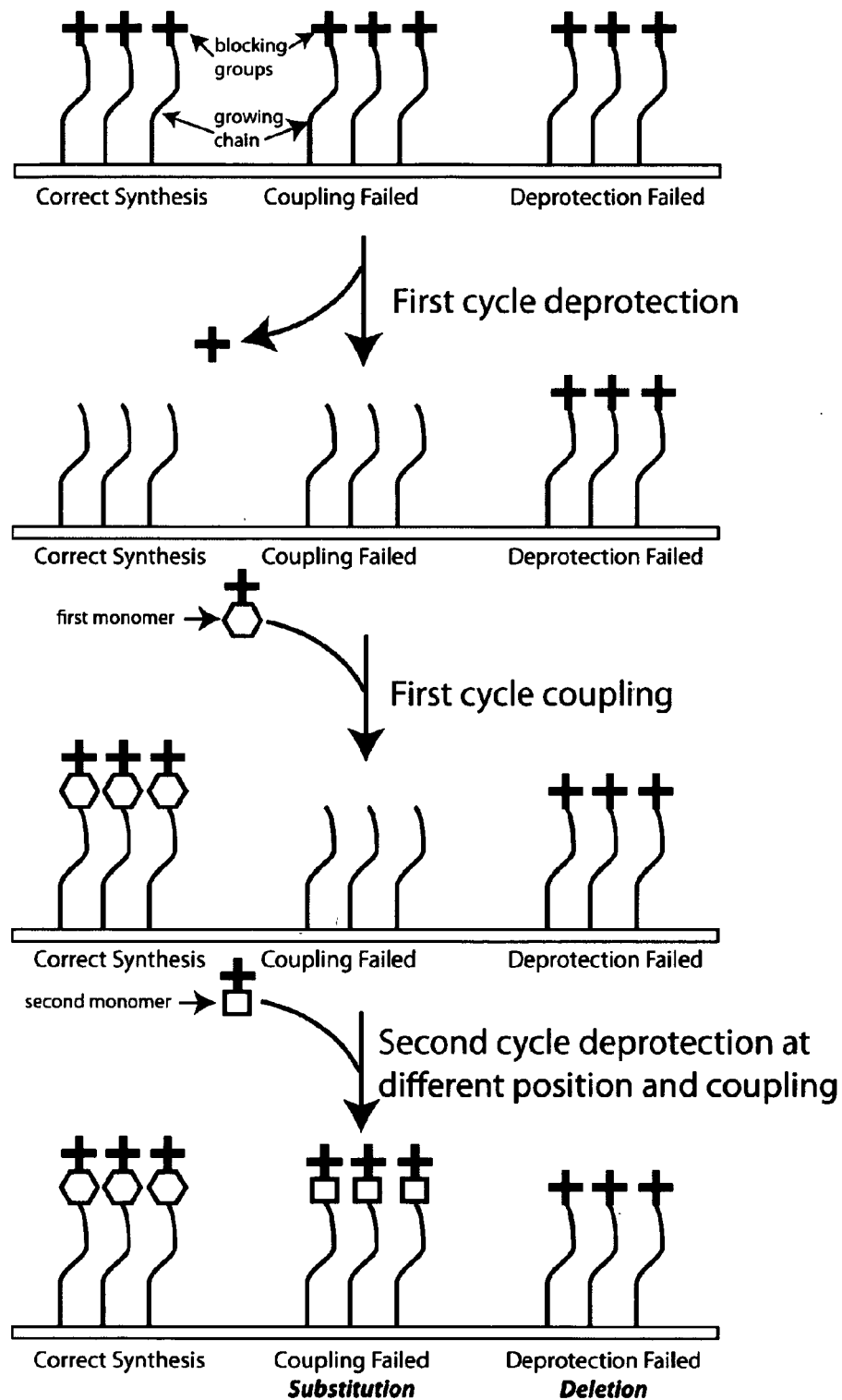
FIG. 2 illustrates an exemplary scheme of a single step reaction corresponding to each cycle in the fabrication. If deprotection failed, the amino acid would not be present (deletion). If coupling failed, an amino acid would be present but it would be the wrong one.

Another useful approach (and these can be performed together in the same QC region) is to make a series of specific short peptides that between them contain each of the steps in a systematic arrangement. The advantage of this approach is two-fold. First, while mass spectrometry is very accurate, even a very specific mass is not necessarily unique: isoleucine and leucine have the same molecular weight, different combinations of two or three amino acids can generate the same molecular weight and a peptide that should have two glycine resides (for example), but only has one, could have had a deletion at either of the two steps. Second, it allows a more consistent comparison of each cycle if they are all performed in a consistent manner. There are many ways that one could devise a systematic set of peptides that would test each cycle sequentially and would allow one to analyze failures in terms of deprotection or coupling. For example, one could simply run a single step reaction corresponding to each cycle in the fabrication. If deprotection failed, the amino acid would not be present (deletion). If coupling failed, an amino acid would be present but it would be the wrong one. An exemplary scheme is shown in FIG. 2.

Figure 3:
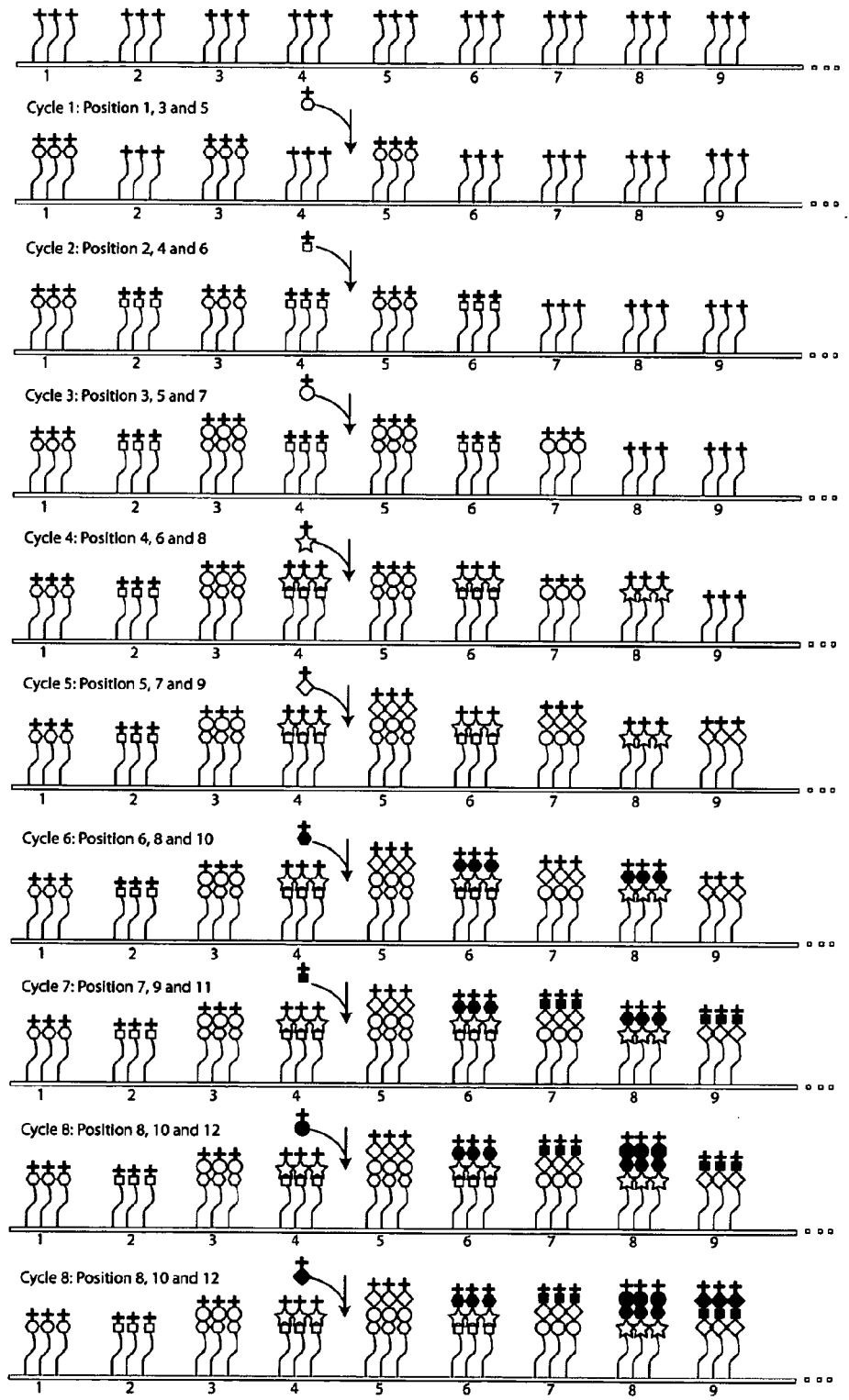
FIG. 3 illustrates one example of a more complex and informative schemes can also be devised; cycle 5 is shown.
Figure 4:
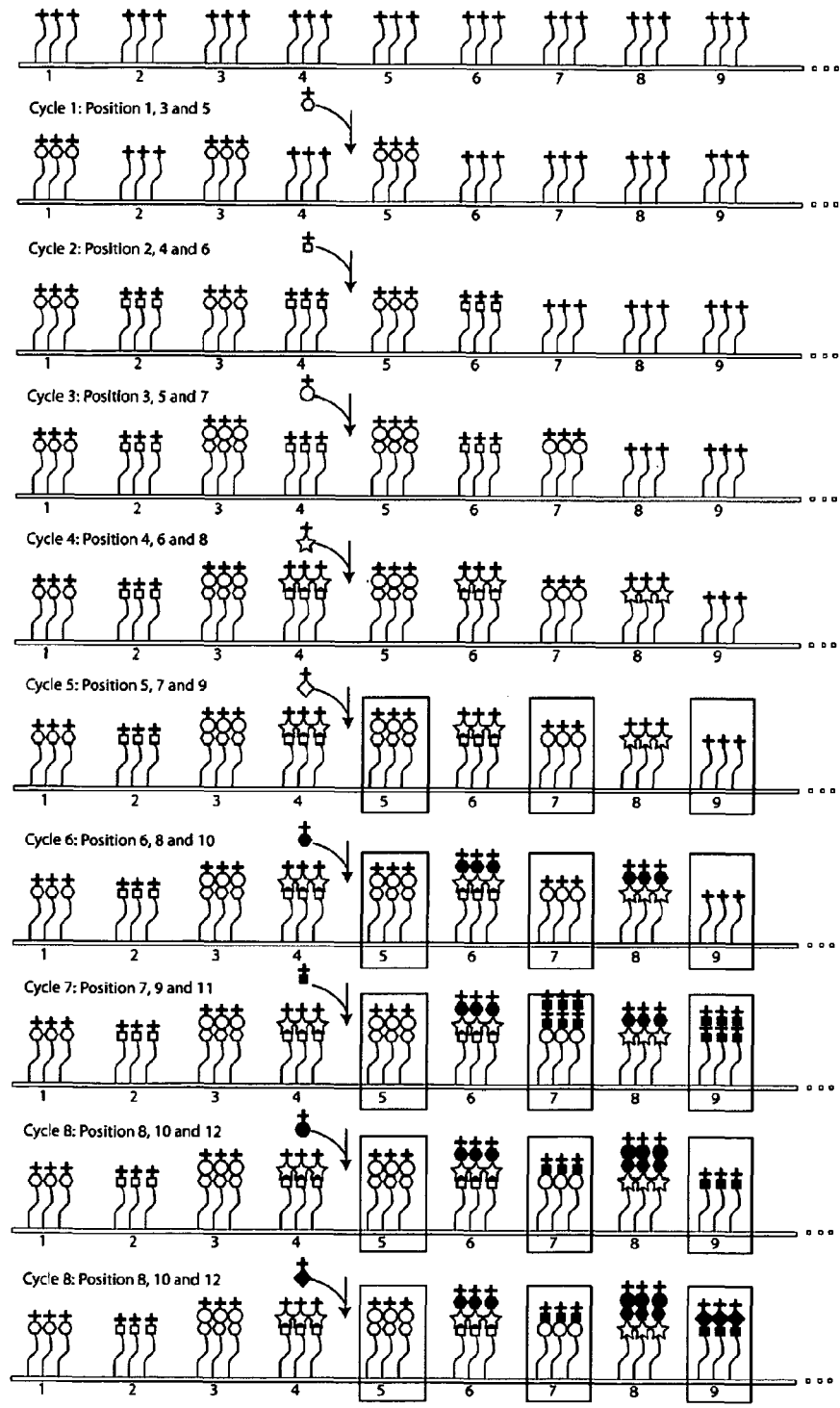
FIG. 4 illustrates what happens if there is a failure of the photodeprotection in cycle 5 compared to FIG. 3.
Figure 5:
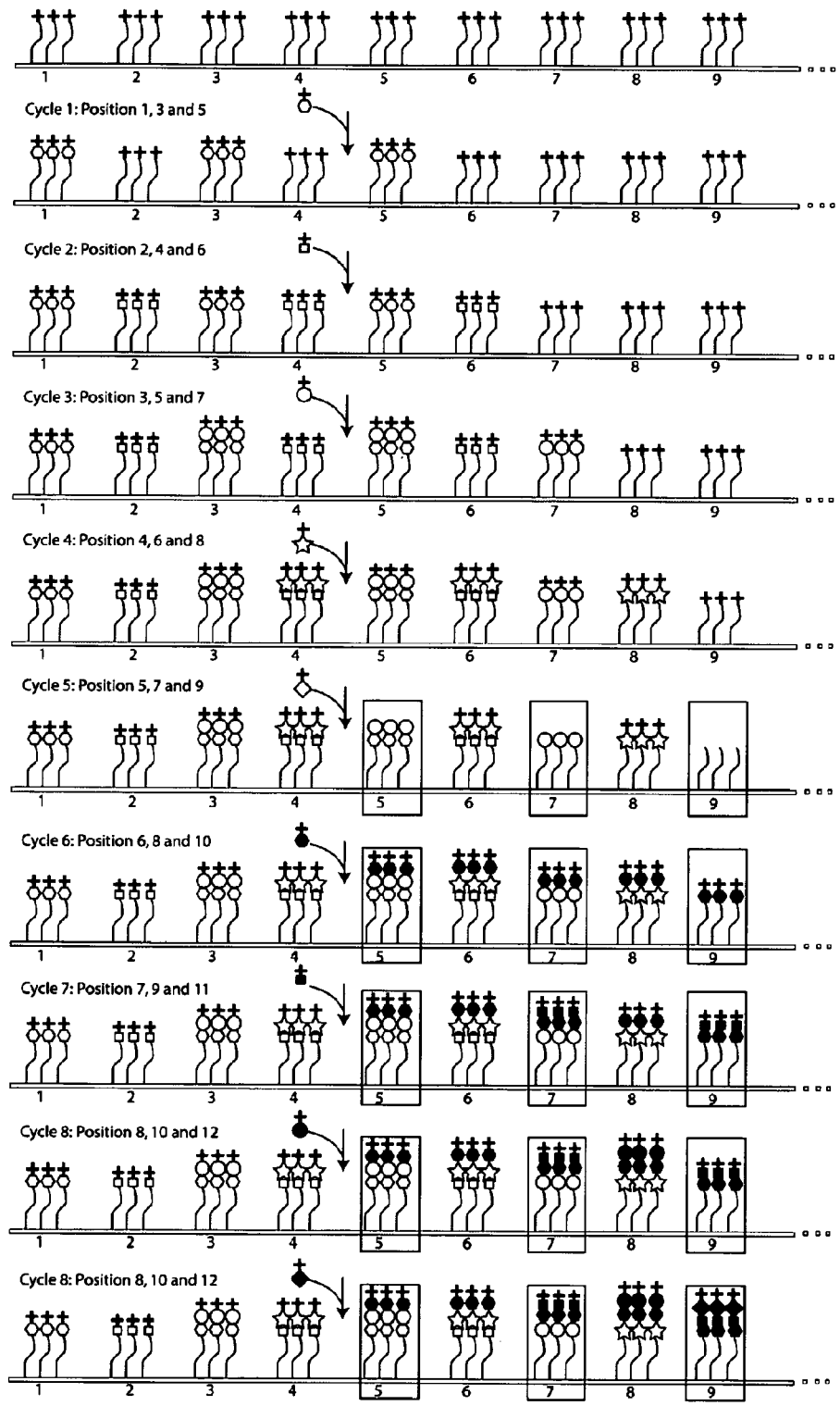
FIG. 5 illustrates what happens if there is a failure of the coupling in cycle 5 compared to FIG. 3.

More complex and informative schemes can also be devised. One nonbinding example is shown in FIGS. 3-5. The approach is as follows: in each cycle (a cycle corresponds to one patterned deprotection and subsequent coupling) three QC features are exposed.

In the example shown, features 1, 3 and 5 are exposed in cycle 1. In the next cycle, three different features are exposed (2, 4 and 6). In the next cycle, 3, 5 and 7 are exposed, then 4, 6 and 8, continuing in that pattern. Every cycle adds an amino acid to three different peptides. From cycle 5 onward, the three peptides are all trimers and the amino acid added is added in the first position of one trimer, the second position of the next trimer and the last position of the final trimer. Consider cycle 5 in FIG. 3. The amino acid added in this cycle is represented as an open diamond. It ends up being the final amino acid in the trimer at position 5, the second to last amino acid at position 7 and the first amino acid in the trimer at position 9. This allows one to ensure that the cycle is functioning properly in multiple sequence contexts.

FIG. 4 shows what happens if there is a failure of the photodeprotection in cycle 5. Note that in this case there is a simple deletion: all of the amino acids represented by the open diamonds disappear, resulting in the formation of dimers rather than trimers.

FIG. 5 shows what happens if there is a failure of the coupling in cycle 5. In this case, the uncoupled, but unblocked, position is left open and the amino acid from cycle 6 is substituted for the one that was supposed to be added in cycle 5. This is true for all three trimers. This brings up another advantage in building the QC region by exposing every other position in this way. Had one exposed 1, 2 and 3 first then 2, 3, 4, etc., a failure of coupling would have generated a deletion, just as the failure in photodeprotection did.

Another advantage of having the every other feature exposure pattern is that if there is cross-talk, for example, if exposure of position 5 also deprotected position 6 (for example, due to a misalignment), this would appear as an insertion at position 6 with the amino acid added in cycle 5 and would be distinct from either failure of photodeprotection or failure of coupling.

In addition to a systematic set of peptides designed to represent each chemical synthesis step, MALDI mass spectrometry enables one to perform oligomer fragmentation analysis. In one example of this, a particular peptide peak of interest (parent) present on the array feature is selected for MALDI tandem mass spectrometry analysis. The parent peptide is fragmented in the MALDI mass spectrometer and each fragment produced is detected. With this fragmentation information, the exact linear or branched sequence of amino acids present in the parent peptide can be identified. This allows one to distinguish peptides that have the same amino acid composition and/or molecular weight, but have different linear or branched arrangements.

Releasing Peptides from the Surface without Diffusion.

To perform the kinds of QC analyses described above, peptides are released from the surface after synthesis without allowing them to diffuse outside of the region they were produced. Patterned synthesis of molecular systems on a surface and release without positional diffusion has many other potential uses as well. This means that one cannot use any kind of liquid agent with droplets having a diameter larger than to the array feature size/pitch in the release. To do this, one uses a linker that is cleavable between the peptide and the surface. Most of the cleavable linkers are either acid labile, base labile or light labile. Some (e.g., safety catch linkers) require two step reactions for release, but the second reaction is typically acid, base or light.

One can use volatilized, nebulized or sublimated acids and bases for this purpose or UV light exposure. In the case of photopatterned synthesis, using a photocleavable linker would need to require a very different wavelength than the wavelength used for photopatterning. Volatile, nebulized or sublimated acids (e.g., TFA, HF, HCl, $H_2SO_4$, HBr, etc.) can be used, particularly for releasing, for example, Fmoc-based heteropolymers such as peptides, as the peptides are not exposed to strong acid during the synthesis.

For syntheses involving acid labile protective groups such as t-Boc amino or trityl groups, an acid labile linker could be cleaved during the synthetic cycling that involves acid production to remove the protecting group (e.g., t-Boc or trityl), thus a volatile, nebulized or sublimated base (ammonia gas being most obvious) can be used.

Figure 6:
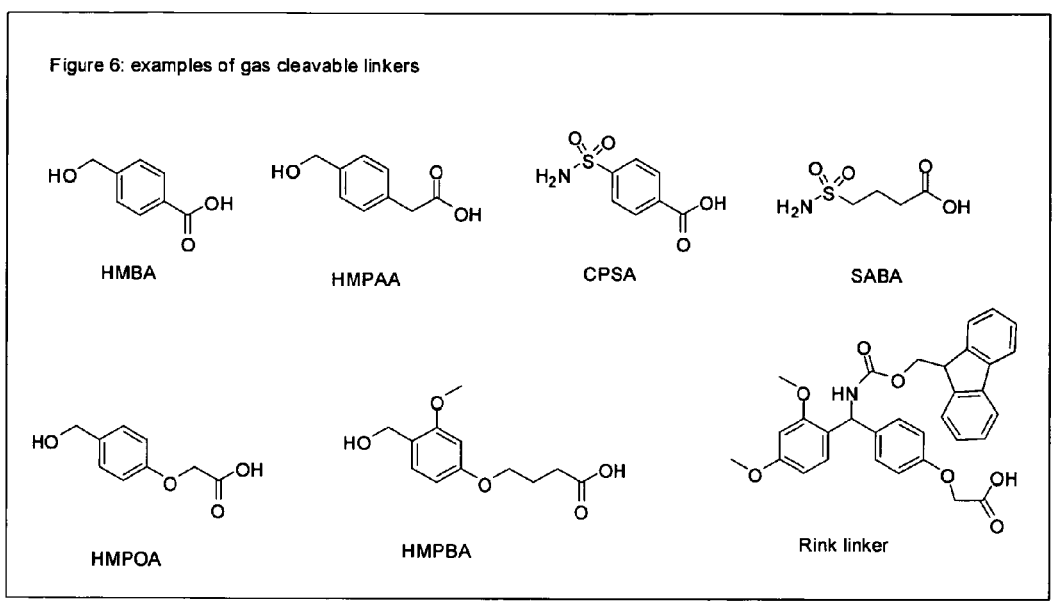
FIG. 6 illustrates appropriate gas cleavable linkers for releasing peptides from the surface without diffusion.

Appropriate linkers include hydroxymethylbenzoic acid (HMBA), hydroxymethylphenylacetic acid (HMPAA), hydroxymethylphenoxyacetic acid (HMPOA), 4-(4-hydroxymethyl-3-methoxyphenoxyl)-butyric acid (HMPB), carboxyproanesulfonamide (CPSA), sulfamoylbenzoic acid (SABA) (and other safety-catch linkers), p-{(R,S)-a-[1-(9H-Fluoren-9-yl)-methoxyformamido]-2,4-dimethoxybenzyl}-phenoxyacetic acid (and variants of the "Rink" linker) (FIG. 6).

Figure 7:
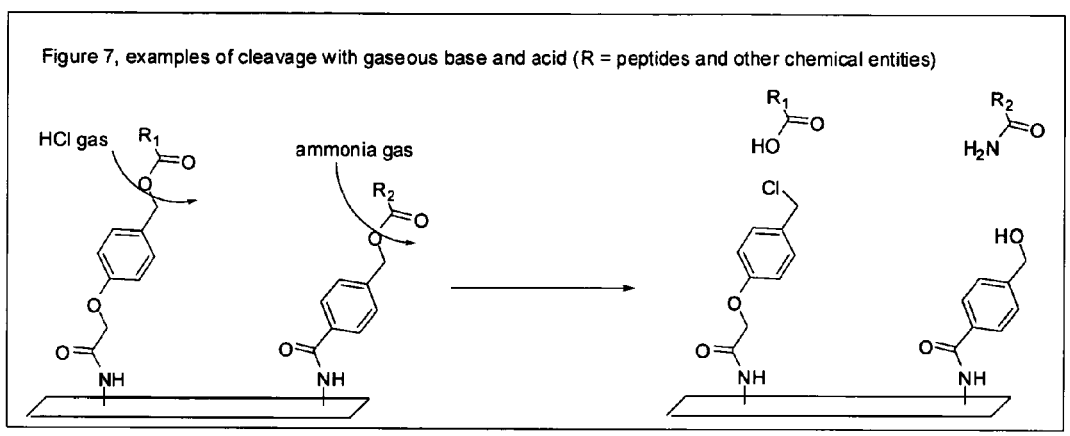
FIG. 7 illustrates examples of cleavage with gaseous base and acid (R=peptides and other chemical entities.

All of these linkers can be cleaved by an appropriate gaseous base (e.g., ammonia) or acid (e.g., HCl, TFA). For example, HMBA and HMPAA linkages can be cleaved by ammonia gas, while HMPOA, HMPBA and the Rink type linkers can be cleaved with HCl gas (FIG. 7).

Figure 8:
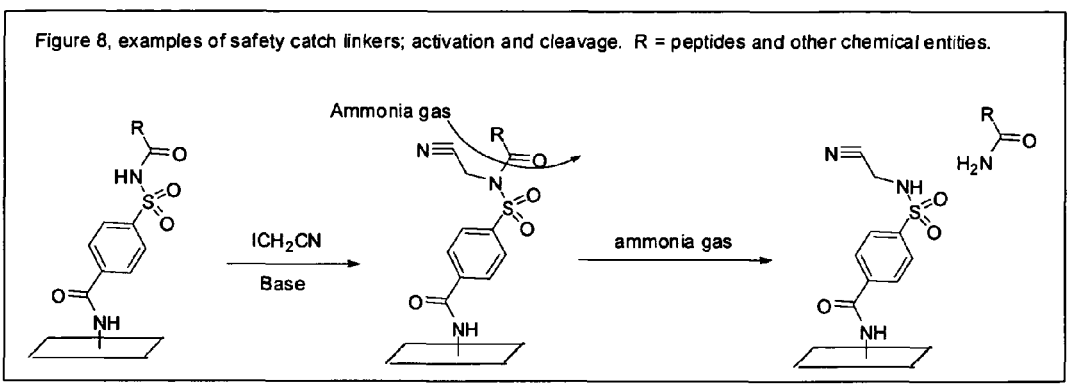
FIG. 8 illustrates examples of safety catch linkers, activation and cleavage. R=peptides and other chemical entities.

The safety catch linkers are stable to base and acid; after a proper chemical modification step, the linkages become cleavable with ammonia gas (FIG. 8).

Enhancing MALDI Sensitivity

Figure 9:
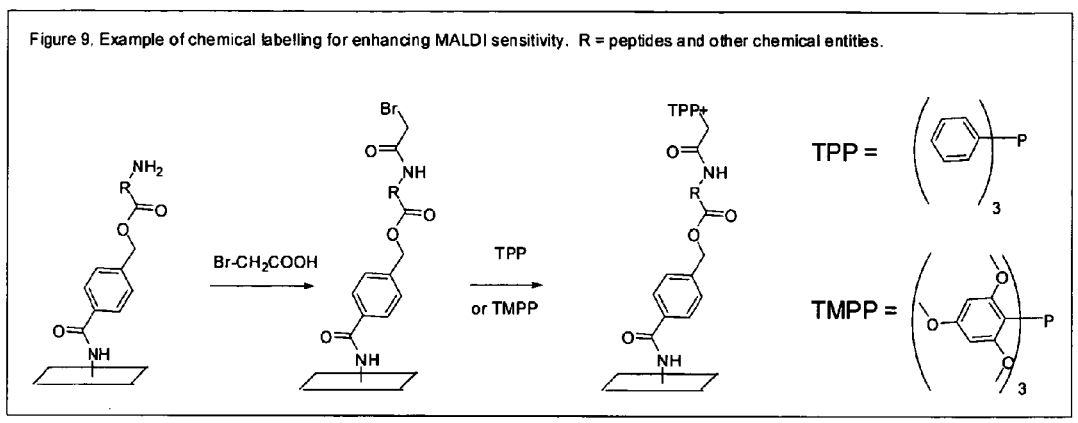
FIG. 9 illustrates an example of chemical labeling for enhancing MALDI sensitivity. R=peptides and other chemical entities.

It is very useful to enhance the sensitivity of the MALDI by coupling a permanently ionized group to the molecule to be measured. There are a number of such molecules that can be coupled to a free amine on a peptide or that can be coupled to the sidechain of an amino acid such as lysine and then inserted into the peptide. Examples include triphenylphosphine (TPP) and its methoxy derivatives such as tris(2, 4,6-trimethoxyphenyl)phosphine (TMPP). In fact, this class of compound can be directly synthesized onto a free N-terminal amine in two steps (FIG. 9): 1, the N-terminal amines are acylated with bromoacetic acid, and, 2, the bromine atom is then displaced with phosphines such as TPP and TMPP to form a phosphonium function, or with tertiary amines such as triethylamine (TEA) to form an ammonium function, both type of functions result in a permanent cation.

Figure 10:
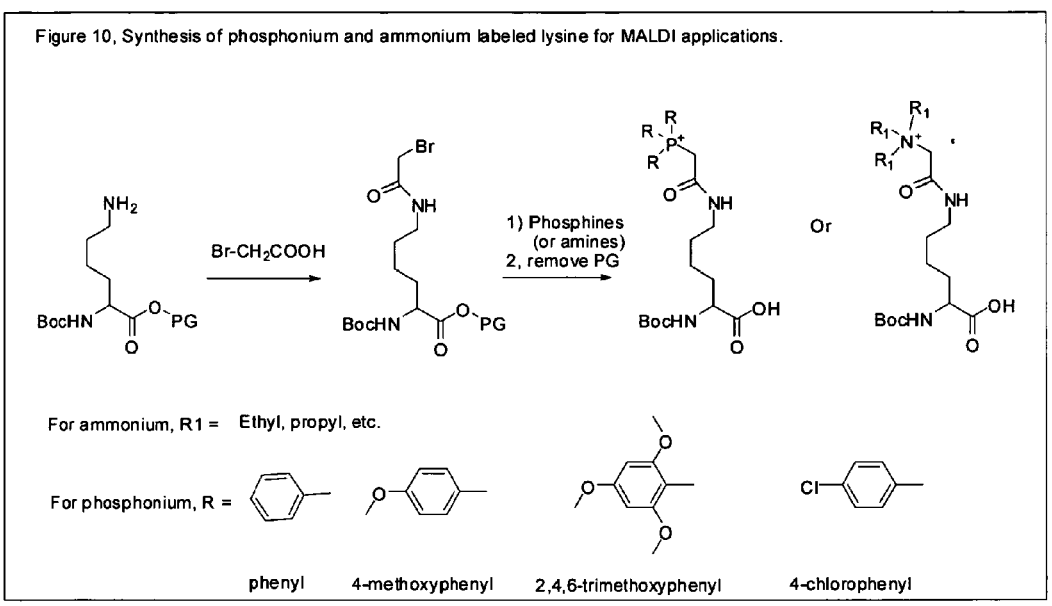
FIG. 10 illustrates synthesis of phosphonium and ammonium labeled lysine for MALDI applications. R=peptides and other chemical entities.

The same process can be used for the modification of the lysine side chain amino group. The phosphonium and ammonium labeled amino acid can be inserted at the C-terminal or any other positions of peptides (FIG. 10).

Integrating Non-Diffusional, Cleavable Linker Strategies with Enhanced MALDI Sensitivity and Specificity.

MALDI mass spectrometry detects positively or negatively charged species, and this mode of detection can be utilized to substantially enhance signal-to-noise and quantitative capabilities. For example, the synthesized array products can be designed or modified to incorporate a fixed positive charge so that a separate ionization process does not have to occur for detection at the time of MALDI desorption from the surface. Placing a fixed charge on each array synthesis product normalizes the signal intensity across multiple synthesis products thereby allowing one to accurately compare product amounts relative to each other by simply comparing MALDI signals from those products.

MALDI mass spectrometry also has high chemical specificity given that many individual peaks can be resolved in a single spectrum and that tandem mass spectrometry can be performed on parent analyte fragments that serve as a fingerprint for specific parent products.

Linkers between the array substrate and the synthesized array molecules can be designed to substantially enhance the detection sensitivity, specificity and quantitative capability. Such a linker would have three characteristics: (1) the ability to cleave from the surface without diffusion on the order of the feature diameter/pitch; (2) the ability to readily ionize, or maintain a fixed charge, during or before MALDI desorption; and (3) the ability to produce a characteristic signal or pattern in the parent mass spectrum and/or fragmentation mass spectrum.

Figure 11:
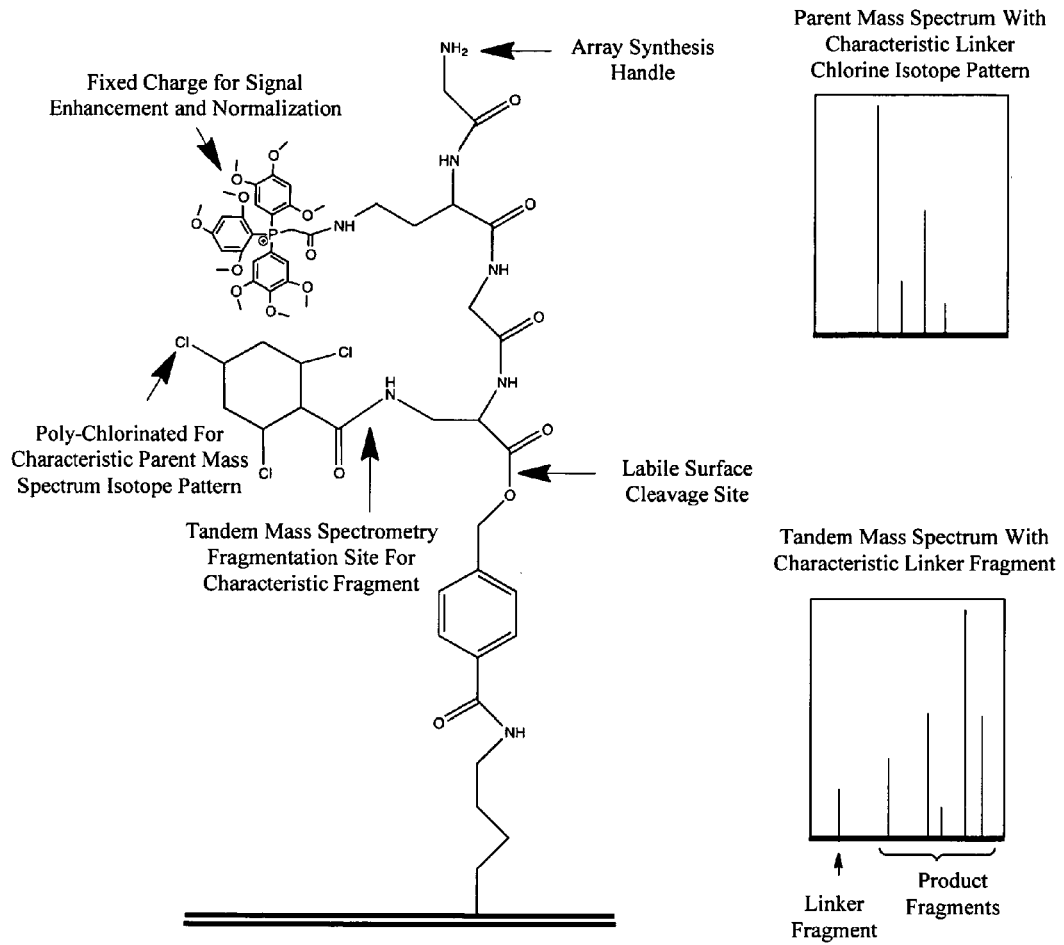
FIG. 11 provides an array synthesis linker with properties that enable high sensitivity and high specificity MALDI characterization of array product composition.

One example of this would be a linker that is base labile (e.g., ammonia gas), with a fixed positive charge covalently attached to the synthesized molecule, and a substituent that produces a characteristic signal in both the parent and fragmentation mass spectra (See, FIG. 11).

Compounds for Use in Arrays

Many different classes of compounds or combinations of classes of compounds can be used for the arrays and methods of the invention. Classes of compounds include nucleic acids and their analogs, polypeptides (broadly defined as above), polysaccharides, organic compounds, inorganic compounds, polymers, lipids, and combinations thereof. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). The test compounds can be natural or synthetic. The compounds can be naturally occurring or nonnaturally occurring. Many different classes of compounds other than nucleic acids can be used, but optionally if the compounds are nucleic acids, the sample components detected are not nucleic acids. In some arrays, the test compounds have a molecular weight of between about 500 and about 10,000 Da, and optionally between about 1000 to about 4000 Da.

The number of compounds used is a balance between two factors. The more compounds, the more likely an array will include members having detectable affinity for any target of interest. However, a larger number of compounds also increases the cost of synthesizing and analyzing an array. Arrays typically have at least 100 compounds. Arrays having between 500 and 500,000 compounds provide a compromise between likelihood of obtaining compounds with detectable binding to any target of interest and ease of synthesis and analysis. Arrays having, for example, 100 to 500,000 members or 500-500,000, or 1000-250,000 members can also be used. Arrays having, for example, between 10,000 and 100,000, between 25,000 and 500,000 or between 50,000 and 350,000 are also contemplated within the disclosures herein. Alternatively, arrays having much larger numbers of members for example, $10^2$-$10^7$ or 1000 to 5,000,000 or 500,000 to 2,000,000 can also be used. Such arrays typically represent only a very small proportion of total structural space, for example less than $10^{-6}$, $10^{-10}$, or $10^{-15}$ in the case of peptides.

Sequence space means the total number of permutations of sequence of a given set of monomers. For example, for the set of 20 natural amino acids there are $20^n$ permutations, where n is the length of a peptide. Although it is widely assumed that most if not all of the residues in a peptide epitope participate in binding to the a target, it is much more likely that between two and five residues in a 10-12 mer epitope are involved in energetically favorable interactions with the target, the other residues are simply there to adjust the positions of the important residues, and to prevent inhibition of binding. Therefore, a relatively small fraction of the total number of possible peptides can provide a good representation of total sequence space, and include members capable of specific, lower affinity interactions with a wide variety of targets. For example, 500-500,000 random peptides can sample the shape space of an immune system ($10^7$ to $10^8$ antibodies in humans) well enough to distinguish between patients with a disease and patients without.

More compounds in the array should allow higher resolution of the diversity of compounds in the complex sample. For example, an array of 1 million compounds should allow more resolution of complex samples, including reflecting the complexity of antibodies in a subject's sample. Yet, even with a much smaller number of compounds, one is able to detect and identify immune responses from infection or immunization.

For polymeric compounds, the lengths of polymers represent a compromise between binding affinity and ease of synthesis. Length of peptides can affect both the affinity and specificity of binding. However, as peptide length increases the chances that any particular binding event will utilize the entire peptide sequence effectively decreases. Cost of synthesis also increases with increasing length while fidelity of synthesis generally decreases. For peptide arrays, peptides having 4-35, 12-35, 15-25 or 9-20 residues are preferred. These ranges of monomer lengths can also be used for other polymers, although aptamers usually have longer lengths (e.g., up to 100 nucleotides).

The compounds (e.g., all or at least 80, 90 or 95%) are typically chosen without regard to the identity of a particular target or natural ligand(s) to the target. In other words, the composition of an array is typically not chosen because of a priori knowledge that particular compounds bind to a particular target or have significant sequence identity either with the target or known ligands thereto. A sequence identity between a peptide and a natural sequence (e.g., a target or ligand) is considered significant if at least 30% of the residues in the peptide are identical to corresponding residues in the natural sequence when maximally aligned as measured using a BLAST or BLAST 2.0 sequence comparison algorithm with default parameters described below, or by manual alignment and visual inspection (see, e.g., NCBI web site ncbi.nlm.nih.gov/BLAST or the like). Because no particular target is used in the design of the arrays (the arrays are designed to broadly cover the space of molecular recognition), essentially any target will bind to the array and form a signature.

Some compounds are randomly selected from total sequence space or a portion thereof (e.g., peptides in which certain amino acids are absent or under-represented). Random selection can be completely random in which case any compound has an equal chance of being selected from sequence space or partially random in which case the selection involves random choices but is biased toward or against certain monomers, such as amino acids. Random selection of peptides can be made for example by a pseudorandom computer algorithm. The randomization process can be designed such that different amino acids are equally represented in the resulting peptides, or occur in proportions representing those in nature, or in any desired proportions.

In some instances, cysteine residues are omitted from library members with the possible exception of a terminal amino acid, which provides a point of attachment to a support. In some libraries, certain amino acids are held constant in all peptides. For example, in some libraries, the three C-terminal amino acids are glycine, serine and cysteine with cysteine being the final amino acid at the C-terminus. A library chosen by random selection, once selected is of known identity and can be reproduced without repeating the initial random selection process. Nevertheless, the compounds in such library retain the same random relations with one another. For example, the peptides in a random library that is subsequently reproduced retain a random distribution throughout sequence space (with the possible exception of cysteine residues, if this residue is omitted). Collections of compounds, such as peptides, that are randomly distributed over sequence space, are still considered random even if reproduced without repeating the initial random selection.

The principles for selecting peptides and other compounds for arrays in the present methods are analogous to those for selecting initial libraries of compounds in producing synthetic antibodies, as further described in WO/2008/048970 and WO2009/140039, the disclosures of which are incorporated by reference in its entirety herein.

Making Arrays

Compounds can be presynthesized and spotted onto a surface of an array or can be synthesized in situ on an array surface (see, e.g., Cretich et al., *Biomol. Eng.* 2, 77-88 (2006); Min et al., *Current Opinion in Chemical Biology* 8, 554-558 (2004), Breitling, *Mol. BioSyst.*, 5, 224-234 (2009), U.S. Pat. No. 5,143,854; EP 476,014, Fodor et al., 1993, Nature 364, 555-556; U.S. Pat. No. 5,571,639, U.S. Pat. No. 5,593,839, EP 624,059, U.S. Pat. No. 6,620,584, and EP 728,520). Customized arrays are also commercially available from suppliers such as Invitrogen, PEPperPRINT, LC Sciences or Pepscan. The surface is usually derivatized with a functional group that attaches to the compounds, optionally via linker Compounds can be attached via covalent or noncovalent linkages. The array surface can be a single contiguous surface of a support.

Alternatively an array can be formed by spotting or synthesizing different compounds on different particulate supports, such as beads. Peptides can be attached in either orientation (N or C) relative to the array. In general, the different compounds occupy different areas of a contiguous array or different particles in a particulate array. The identity of which compound occupies which area of an array or which particle is usually either known as a result of the synthesis process or determinable as a result of an encoding process. Encoding processes are commonly used for beads. The different areas in a contiguous array can be immediately adjoining as may arise when such arrays are the result of in situ synthesis, or separated, which is often the result of spotting.

An area or cell of an array is a unit of surface area from which a separate signal is detectable. In some arrays, each area of the array is occupied only by molecules of the same compound except for possibly a small degree of bleed over from one area to another, due for example, to imperfections in the array. In other arrays, some or all of the areas contain a pool of two or more different compounds. In such an array, the signal from an area containing a pool of two or more different compounds is the aggregate undivided signal from the compounds constituting the pool.

Such arrays typically contain from 100-5,000,000 compounds (e.g., 100-1,000,000, 500, 100,000 or 500-25,000 compounds) as discussed above. These numbers of compounds can readily be accommodated in different regions of an array of the order of 0.1-5 $cm^2$ combined area.

Within any one area of a contiguous array or within any one particle of a particle array many different molecules of the same compound are present. Because compounds are usually attached to a derivatized surface of a support or particle (e.g., a support or particle bearing a linker), the density of molecules within an area of an array or a particle can be controlled in part by the derivatization process, for example, the period of time and concentration of derivatizing agent used. The density of molecules can also be controlled by the attachment or in situ synthesis process by which a compound is attached to a support. The length of a coupling cycle and concentration of compound used in coupling can both affect compound density.

The density of different molecules of a compound within an area of an array or on a particle controls the average spacing between molecules of a compound (or compounds in the case of a pooled array), which in turn determines whether a compound is able to form enhanced apparent affinity to a sample (an avidity interaction). If two molecules of a compound or compounds in the case of a pooled array, are sufficiently proximate to one another, both molecules can enhance apparent affinity to the same binding partner. For peptides of length 15-25 residues an average (mean) spacing of less than 0.1-6 nm, 1-4 nm, 2-4 nm, e.g., 1, 2 or 3 nm is, for example, suitable to allow different regions of the same compound to undergo binding with enhanced apparent affinity. Average (e.g., mean) spacings are typically less than 6 nm because spacings of 6 nm or more are do not allow avidity to enhance the apparent affinity for the target or cooperative binding to take place. For example, for peptides of lengths 15-25 residues, the two identical binding sites of one antibody could not span more than 6 nm to contact two peptides at once and bind cooperatively. The optimum spacing for enhancing avidity and/or cooperativity interactions may vary depending on the compounds used and the components of the sample being analyzed.

Enhancement of apparent affinity through either cooperative binding or avidity interactions can be shown by several methods, including comparing binding strength of an antibody to an otherwise identical antibody fragment (e.g., a Fab fragment) having only one binding site. Binding strength to the intact antibody that is greater than the antibody fragment (e.g., higher apparent association constant) may differentiate cooperativity from enhanced avidity. Enhancement of binding strength can also be shown by comparing the binding of an array of an immobilized compounds to an intact antibody with two binding sites with the reverse format in which the antibody is immobilized and the compound is in solution. Stronger binding (e.g., higher apparent association constant) of the immobilized compound to the antibody in solution compared with immobilized antibody to the compound in solution provides an indication that the immobilized compound can either form multivalent bonds to the antibody (cooperative binding), or interacts via enhanced avidity. Association constants, or apparent association constants, of compounds can be measured by conventional methods using technologies like SPR, ELISA, Luminex and other solution-phase binding (e.g., monitoring changes in bound signal over time) when the antibody or other sample is immobilized and the compound is in solution. Conversely, apparent association constants can be measured when a compound is immobilized and antibody or other sample is in solution. Once suitable synthesis or deposit conditions have been established for achieving arrays capable of enhanced binding, other arrays can be made under the same conditions without individualized testing. Usually, different compounds are deposited or synthesized in different areas of an array under the same conditions, so that if one compound is spaced so that it is capable of enhanced avidity binding, most or all compounds are. In some arrays, at least 10%, 50%, 75%, 90% or 100% of compounds in the array are spaced so as to permit enhanced avidity interactions and/or undergo cooperative binding with a binding partner. However, it is not necessary that all compounds be deposited or synthesized with the same spacing of molecules within an area of the array. For example, in some arrays, some compounds are spaced further apart so as not to permit or permit only reduced avidity interactions or cooperative binding compared with other compounds in an array.

The spacing can be measured experimentally under given conditions of deposition by depositing fluorescently labeled compounds and counting photons emitted from an area of an array. The number of photons can be related to the number of molecules of fluorescein in such an area and in turn the number of molecules of compound bearing the label (see, e.g., U.S. Pat. No. 5,143,854). Alternatively, the spacing can be determined by calculation taking into account the number of molecules deposited within an area of an array, coupling efficiency and maximum density of functional groups, if any, to which compounds are being attached. The spacing can also be determined by electron microscopy of an array or via methods sensitive to the composition of molecules on a surface such as x-ray photoelectron spectroscopy or secondary ion mass spectrometry.

Arrays having larger spacing that do not permit cooperative binding or avidity interactions or do so to a reduced extent compared with spacing described above also have application in identifying high affinity interactions. This type of strategy can be used to identify peptides or other compounds, for example, that are very close structurally to the original epitope that raised the antibody response. Alternatively, for arrays of peptides from life space (the set of amino acid sequences represented in the proteins of living organisms), this spacing facilitates identifying the true epitope.

The spacing between compounds can also be controlled using spaced arrays; that is, arrays on surfaces coated with nano-structures that result in more uniform spacing between compounds in an array. For example, NSB Postech amine slides coated with trillions of NanoCone apexes functionalized with primary amino groups spaced at 3-4 nm for a density of 0.05-0.06 per $nm^2$ can be used.

Array formats that can be used include microarrays, beads, columns, dipsticks optical fibers, nitrocellulose, nylon, glass, quartz, mica, diazotized membranes (paper or nylon), silicon, silicones, polyformaldehyde, cellulose, cellulose acetate, paper, ceramics, metals, metalloids, semiconductive materials, quantum dots, coated beads, other chromatographic materials, magnetic particles; plastics and other organic polymers such as polyethylene, polypropylene, and polystyrene; conducting polymers such as polypyrole and polyindole; micro or nanostructured surfaces, nanotube, nanowire, or nanoparticulate decorated surfaces; or porous surfaces or gels such as methacrylates, acrylamides, sugar polymers, cellulose, silicates, and other fibrous or stranded polymers.

An exemplary method of array preparation is as follows. A microarray is prepared by robotically spotting distinct polypeptides on a glass slide having an aminosilane functionalized surface. Each polypeptide has a C-terminal glycine-serine-cysteine as the three C-terminal residues and the remaining (17) residues determined by a pseudorandom computational process in which each of the 20 naturally occurring amino acids except cysteine had an equal probability of being chosen at each position. Polypeptides are conjugated to the aminosilane surface by thiol attachment of the C-terminal cysteine of the polypeptide to a maleimide (sulfo-SMCC, sulfosuccinimidyl 4-[N-maleimidomethyl] cyclohexane-1-carboxylate which is covalently bonded to the aminosilane surface. The polypeptides are chemically synthesized, dissolved in dimethyl formamide at a concentration that may range from about 0.1 mg/ml to about 2 mg/ml, and then diluted 4:1 with phosphate-buffered saline prior to spotting. The concentration of peptide or other compound determines the average spacing between peptide molecules within a region of the array. A concentration of 1 mg/ml gives an average spacing of about 0.5 nm. The spacing decreases non-linearly with dilution at lower concentrations. The printed slides stored under an argon atmosphere at 4° C. until use.

An exemplary calculation of spacing is as follows: spot size: 150 μm, spot area: 17671 $μm^2$, nanoprint deposition volume: 200 pL, peptide concentration: 1 mg/ml, deposition amount: 200 pg, # peptides deposited: $8 \times 10^{10}$ per spot, $8 \times 10^{10}$ peptides/17671 $μm^2 = 4.5 \times 10^6$ peptides/$μm^2$, $2.2 \times 10^{-7}$ $μm^2$ area needed by 1 peptide ($4.6 \times 10^{-4}$ μm spacing).

As well as including compounds randomly or without regard to the sample being analyzed, arrays can include other compounds known to bind particular targets, such as proteins, in a sample. These compounds can be antibodies, synbodies or peptides among others. Usually, such interactions are high affinity (e.g., greater than $10^7$, $10^8$ or $10^9$ $M^{-1}$). The number of such known binding partner compounds can be large, for example, there can be a different compound for at least 25, 50, 75, or 90% or substantially all of the known proteins expressed by a given genome, such as the human genome). The different known binding partner compounds occupy different areas of the array in similar fashion to randomly selected compounds. However, because the known binding partner compounds are in general capable of high affinity interactions, they can be used with or without an intermolecular spacing that permits enhanced avidity interactions with the sample. Although one might think that inclusion of compounds selected at random or without regard to the sample being analyzed would be redundant in view of inclusion of known binding proteins to a large part or all of the encoded proteins in a genome, such is not the case because some diagnostic immune responses are the result of somatic mutation or non-protein components and not detected by binding proteins to encoded proteins.

Samples and Components to be Analyzed

The arrays and methods of the invention can be used for analyzing any kind of sample containing or potentially containing analyte(s) of interest. Of particular interest are samples from human or veterinary patients or laboratory model animals. Such samples can be blood (including whole blood, red cells, plasma and the like), urine, feces, saliva, CNS fluid, other body fluids, hair, skin, biopsies and the like. A profile can be obtained from a small volume of sample, e.g., less than, or equal to, for example, 1 µl. Some samples are from patients known or suspected to be suffering from a disease. The identity of the disease may or may not be known. Some samples are obtained from patients known to have been subjected to a risk of disease but in which symptoms of disease are not yet evident. The risk can be genetic (e.g., a particular gene or family history) or experiential (e.g., exposure to a toxic chemical or radiation). Samples can also be obtained from patients who have been vaccinated to analyze the resulting immune response.

Samples from patients can include a wide variety of components subject to potential analysis by an array. The components most amenable to detection are those capable of enhanced avidity interactions to compounds in the array. Such components include antibodies, which can support avidity interactions and/or support cooperative binding through their pairs of heavy and light chains (i.e., two binding sites per antibody) and cells, which can form multiple bonds through multiple copies of receptors displayed from their outer surfaces. Viruses can also form enhanced binding interactions through different copies of coat proteins on their outer surface. Samples from patients can include many different antibodies and/or different cells and/or other components.

Samples can be analyzed with little if any further processing or can be subject to further processing such that only selected components of the sample (e.g., antibodies or cells) are analyzed with the array.

Methods of Detection

Binding interactions between components of a sample and an array can be detected in a variety of formats. In some formats, components of the samples are labeled. The label can be a radioisotype or dye among others. The label can be supplied either by administering the label to a patient before obtaining a sample or by linking the label to the sample or selective component(s) thereof.

Binding interactions can also be detected using a secondary detection reagent, such as an antibody. For example, binding of antibodies in a sample to an array can be detected using a secondary antibody specific for the isotype of an antibody (e.g., IgG (including any of the subtypes, such as IgG1, IgG2, IgG3 and IgG4), IgA, IgM). The secondary antibody is usually labeled and can bind to all antibodies in the sample being analyzed of a particular isotype. Different secondary antibodies can be used having different isotype specificities. Although there is often substantial overlap in compounds bound by antibodies of different isotypes in the same sample, there are also differences in profile.

Binding interactions can also be detected using label-free methods, such as surface plasmon resonance (SPR) and mass spectrometry. SPR can provide a measure of dissociation constants, and dissociation rates. The A-100 Biocore/GE instrument, for example, is suitable for this type of analysis. FLEXchips can be used to analyze up to 400 binding reactions on the same support.

Optionally, binding interactions between component(s) of a sample and the array can be detected in a competition format. A difference in the binding profile of an array to a sample in the presence versus absence of a competitive inhibitor of binding can be useful in characterizing the sample. The competitive inhibitor can be for example, a known protein associated with a disease condition, such as pathogen or antibody to a pathogen. A reduction in binding of member(s) of the array to a sample in the presence of such a competitor provides an indication that the pathogen is present.

The stringency can be adjusted by varying the salts, ionic strength, organic solvent content and temperature at which library members are contacted with the target.

Applications

The arrays have a wide variety of applications in analyzing or characterizing clinical, veterinary, forensic, laboratory and other samples. As with conventional diagnostics, the arrays can be used to identify particular analytes within samples, for example, analytes associated with particular disease. However, the methods can also be used to provide a binding profile of different compounds characterizing a sample. The binding profile represents the aggregate interactions of the compounds with different components in the sample, and can be characteristic of a particular disease, stage of disease or lack of disease. The different components can be complex (e.g., at least 10, 100, 1000 or 1,000,000,000 different antibodies and/or different cells).

A binding profile typically includes compounds whose interactions with the sample are nonspecific as well as compounds whose interaction with the sample reflect specific but low affinity interactions (i.e., apparent or actual dissociation constant between $10^{-3}$ and $10^{-6}$). Compounds with higher affinity interactions (i.e., dissociation constant less than $10^{-6}$) may or may not be present. Such higher affinity interactions if present may arise by chance as a result of a compound in the array being a mimetic of a natural binding partner of a sample component or as a result of including a control in which a compound is a known binding partner of a component of a sample. However, a sample can usually be adequately characterized by the binding profile of compounds with low affinity interactions with the sample, optionally in combination with compounds lacking specific binding to components of the sample. For example, the identity and relative binding of at least 2, 5, 10 or 50 compounds capable of low affinity specific binding to components of the sample can often be used to characterize the sample. Such low affinities actions may in part be the result of compounds serving as mimetopes providing a linear epitope that (imperfectly) resemble an epitope against which an antibody in the same was raised (e.g., a complex 3D-structure).

One application lies in analyzing samples from patients known or suspected to be suffering from a disease but in which the particular disease affecting the patient is not known. A conventional approach would be to perform separate assays for suspected diseases. By contrast, in the present methods, a single binding profile from the patient sample can be used to characterize the patient for many diseases, stage of disease or lack of disease. The binding profile can be used to characterize the sample for virtually any disease, including autoimmune disease, cancer, infectious diseases, and diseases of the CNS. Most if not all diseases involve some change s in antibodies, cells or other components present in patient samples, reflected in a binding profile. Some exemplary infectious diseases include bacterial, fungal and viral diseases, such as Valley Fever, Q-fever, *Tularemia tularensis, Rickettsia rickettsii*, HSV types I and II, HVB, HVC, CMV, Epstein Barr virus, JC virus, influenza, A, B or C, adenovirus, and HIV. Because different infections give different profiles, different infections in a patient having multiple infections can be detected simultaneously. Some exemplary cancers that can be diagnosed or prognosed using the methods of the invention include glioblastoma, breast cancer, multiple independent primary cancer and/or recurrence situation, pancreatic cancer, lung cancer, myeloma, ovarian cancer and esophageal cancer. Precancerous cells that are morphological distinguishable from normal cells but not yet cancerous can also be detected using the methods of the invention. Neurological diseases, such Alzheimer's disease, although not generally considered to be an autoimmune disease, results in some changes in antibodies present in a sample. The same is the case for chronic diseases, such as Asthma, Rheumatoid arthritis, Diabetes mellitus type 1, Psoriasis, Multiple Sclerosis and others.

Another application lies in analyzing samples from patients known or suspected to have a particular disease, but in which the stage, severity or prognosis for the disease is unclear. Again the binding profile can provide an indication of any of these factors.

Another application lies in analyzing samples from vaccinated patients to determine whether an adequate protective immune response is developing. The pattern of response in one patient can be compared, for example, with a patient who has been naturally infected with the pathogen and survived, a similarity of response pattern indicating the patient is likely to survive and a dissimilarity that the patient will get worse or die at least in the absence of alternate treatment. Alternatively, a profile of a patient or animal model immunized with a new vaccine (for example in a clinical or preclinical trial) can be compared with profiles of patients or control animals immunized with an existing vaccine known to be effective. In a further variation, patients being recruited for a clinical trial of a vaccine can be prescreened for binding profile. Those already having a binding profile similar to that of a patient immunized with a vaccine known to be effective or from a patient who has survived a natural infection can be eliminated from the trial because their inclusion might lead to a misleading placebo response.

Another application lies in screening samples from patients who have undergone organ transplant (particularly allotransplantation). The profile in a patient under test can be compared with profiles of patients undergoing organ transplant who have or have not undergone rejection following the transplant. Similarity of the profile between a patient under test and a patient who has previously undergone rejection (or an average profile of a collection of such patients) indicates that the patient is at risk or is undergoing rejection.

Another application lies in analyzing samples from a patient known to be at risk of a disease but in which symptoms of disease are not yet present. The risk can be genetic, such as a genetic mutation associated with disease or family history of the disease, or arise as a result of experience, for example, exposure to a toxic chemical, radiation, traumatic accident, stress, fatigue, chemotherapy, unprotected sex, age, or exposure to a subject with a contagious disease. Such a patient is naturally concerned about the possibility of acquiring a disease and early therapeutic intervention. The methods are particularly useful in crisis situations in which many subjects have had potential exposure to a risk. Conventional diagnostic assays often have a significant lag period before a disease can be developed. For example, conventional viral assays can take several months to develop detectable patient antibodies. Autoimmune diseases (e.g., lupus, type 1 diabetes, rheumatoid arthritis, multiple sclerosis) can take several years to develop specific autoantibody or T-cell responses to specific autoantigens. By contrast, the present methods can detect changes in a profile within a few days (e.g., less than 10, 5 or 3 days) of exposure to a risk, or infection. The changes in binding profile may reflect subtle changes in concentrations of many different components of a sample, few if any of which would be individually detectable. However, in the aggregate, the changes in binding profile of the compounds in the array indicate a change if the risk has started development of disease.

Another application lies in forensic analysis of a sample, for example, a sample recovered from a crime scene or a sample relevant to a paternity analysis. Comparison of a test sample with one or more references samples of known origin can provide an indication of the source of the test sample.

Binding profiles can be used in a variety of ways in characterizing a sample. In some methods, a binding profile of a sample is compared with one or more reference binding profiles of the same compounds. A reference binding profile is a profile that characterizes a particular disease, stage of disease or lack of disease, and the like. Reference profiles are typically determined by averaging binding profiles of several samples (e.g., at least 2, 20, 50 or 100) each characterized for the same disease, stage of disease or lack of disease. Comparison of a sample binding profile with a reference binding profile can involve comparing the different binding strengths of different compounds in an array to the respective samples to derive a value representing the overall similarity of the profiles. A measure of similarity on a scale of similarity is by implication an inverse measure of disimilarity and vice versa. Thus, a value representing the overall similarity includes a value representing the overall disimiliarity. However, mathematically disimiliarity matrices can be handled and analyzed distinctly from similarity matrices. Raw data from the sample being analyzed can of course be normalized before the comparison to eliminate any differences due to sample size, processing, concentration and the like, rather than relative representation of sample components. Standard ANOVA analyses can also block such nuisance factors, provided such factors are accounted for in the experimental design.

Various techniques can be used to derive a value based upon the comparison of a binding profile and a reference binding profile. A derived value can be used to measure the dissimilarity between the binding profile and the reference profile and be evaluated using a distance measure such as the Euclidean Distance (ED) metric. The ED metric is typically used for measuring the distance between two vectors of "n" elements. According to one implementation, if $x=(x_1, x_2, x_3, \ldots, x_N)$ and $y=(y_1, y_2, y_3, \ldots, y_N)$ are two points in Euclidean N-space, then the Euclidean distance between x and j may be computed as:

$$D_{xj} = \text{SquareRoot}(\text{Summation}((x_i - y_i)^2))$$

The ED metric thus not a correlation (0 to 1), but a measurement of dissimilarity.

In the context of comparing a binding profile (defined by its binding values for each point in N-dimensional space, where N is the number of experimental points (conditions)) with a reference binding profile, a ED metric can be determined regardless of the complexity, number of peptides, or number of patients. Each profile being compared may be seen as a pattern: setting an explicit series of points across time, across dilutions, across disease states, across symptoms, etc., and the comparison described here looks for data that reflects this defined series of points.

To standardize the difference between binding profiles being compared, the calculated ED measurement may be normalized by dividing by the square root of the number of conditions as follows:

$$\text{Distance} = |a-b|/\text{square root of } N$$

This is distinct from the aforementioned distance calculation by normalizing for the total number of conditions. This prevents the distance calculation from expanding too far given large numbers of samples.

Accordingly, calculating the Euclidean distance between two data points involves computing the square root of the sum of the squares of the differences between corresponding values. Because the ED metric is a measure of dissimilarity, the distance (d) may be converted, when needed, to a similarity measure as $1/(1+d)$. Distance, similarity, and dissimilarity are interchangeable to a certain degree but each is a uniquely useful given the calculations being applied. As the distance gets larger, the similarity gets smaller. This renders the original data useful for looking at differences in a non-biased and geometrical way. The computation is scalable with increasing number of experiments. In fact, the complexity of the pattern is inherently diminished to the calculation because it is in the denominator and is a square root.

Other distance metrics that can be used include Euclidean Squared, Pearson Correlation, Pearson Squared, Spearman Confidence or Correlation, and other like techniques.

Binding profiles can also be used in various analytical methods to further characterize the sample. For example, a compound in the array showing relatively strong binding to the sample (compared with other compounds in the array) can be used to affinity purify a component of the sample. The component can then be further characterized (e.g., by sequencing or immunoreactivity). The identity of the compound may be characteristic of a disease state (e.g., a pathogen, autoantibody or tumor associated antigen). If the component is not already known to be characteristic of a disease state, it can be used as a new target for developing therapies or diagnostics against the disease state. For example, autoantigens or peptides thereof, can be used in inducing tolerance of autoimmune disease. Alternatively, after washing off unbound cellular components, the cellular components binding to an array can be dissociated from the array, fractionated and analyzed in similar fashion. In a further variation, the identity of a compound in the array showing relatively strong binding to a sample can be used to identify a ligand of the component bound in the sample, and hence the component in the sample. For example, if the compounds of the array are peptides, the sequence of a peptide showing relatively strong binding to a sample can be compared with a database of protein sequences. Comparison can be pairwise between a database sequence and a peptide in the array or between a database sequence and a motif or consensus sequence from a plurality of peptides in the array. Sequence similarity to a protein in the database provides an indication that the protein is a ligand of the component in the sample to which the peptide showed strong binding. The identity of a ligand in turn provides at least an indication of potential molecules in the sample and in turn disease states characterized by such molecules.

The same array can be used in any of the applications described above and for virtually any disease or suspected disease state. The same array means either literally the same array, in which case the array may be washed between different samples, or different copies of an array of the same composition. The identity of which compounds in the array are most informative for a disease or other state being analyzed varies by state. Thus, having identified the most informative compounds for a particular disease, derivative arrays or other detection devices and kits can be made that have a reduced number of compounds including the most informative compounds. The derivative arrays are sometimes referred to as secondary arrays to distinguish them from primary arrays used in initial identification of binding compounds and sometimes a sample component bound by these compounds.

A further useful aspect of the present methods is that they can detect not only increased binding of compounds to cellular components in test samples relative to a control sample representing an undiseased subject (typically a human) but can also detect decreases. For example, some sample components, particularly antibodies, can be detected to decrease in a test sample, such as a disease or vaccinated sample or any other of the samples types mentioned, and other sample components increase.

Derivative Analyses

In addition to being useful in themselves for analyses of samples as discussed above, the present methods are also useful for determining derivative compounds and detection devices. In a simple form of such methods, a derivative device or other array in constructed containing one or more compounds known to be associated with a given disease, susceptibility to disease or other condition described above, and omission of other compounds from the primary array not found to be informative for this disease, susceptibility or other condition. In some such methods, only a small proportion of the compounds used in a primary array (e.g., less than 0.1%, 1% or 5% are retained). In other methods, a component of the sample bound by some of the compounds in a primary array is identified by any of the approaches discussed in the previous section. Having identified a component of the sample, one or more known binding partners of the component are also identified. The known binding partners can be compounds from the primary array, antibodies to the component or other compound, such as a synbody that is known to bind to the component. The known binding partner(s) can then be used to detect the sample component to which they are known to being by any otherwise conventional diagnostic assay. For example, if the known binding partner is an antibody, the assay can be an ELISA, immunoprecipitation, radioimmunoassay or the like. If a plurality of known binding partners are used, the known binding partners can be immobilized in an array format. The known binding partners can also be incorporated into diagnostic kits or diagnostic device (e.g., attached to a support). Such arrays, diagnostic devices and kits can be manufactured by conventional means. Of course, once the known binding partners of a component have been identified, it is not necessary to repeat the initial screening with the primary array for subsequent manufacture of such arrays, diagnostic devices and kits.

Although the embodiments have been described with reference to the presently preferred embodiments, various modifications can be made without departing from the invention. Unless otherwise apparent from the context any step, element, embodiment, feature or aspect of the embodiments can be used with any other.

EXAMPLES

Example 1: MALDI-TOF Image of a Quality Control (QC) Region of a Silicon Wafer

Figure 12:
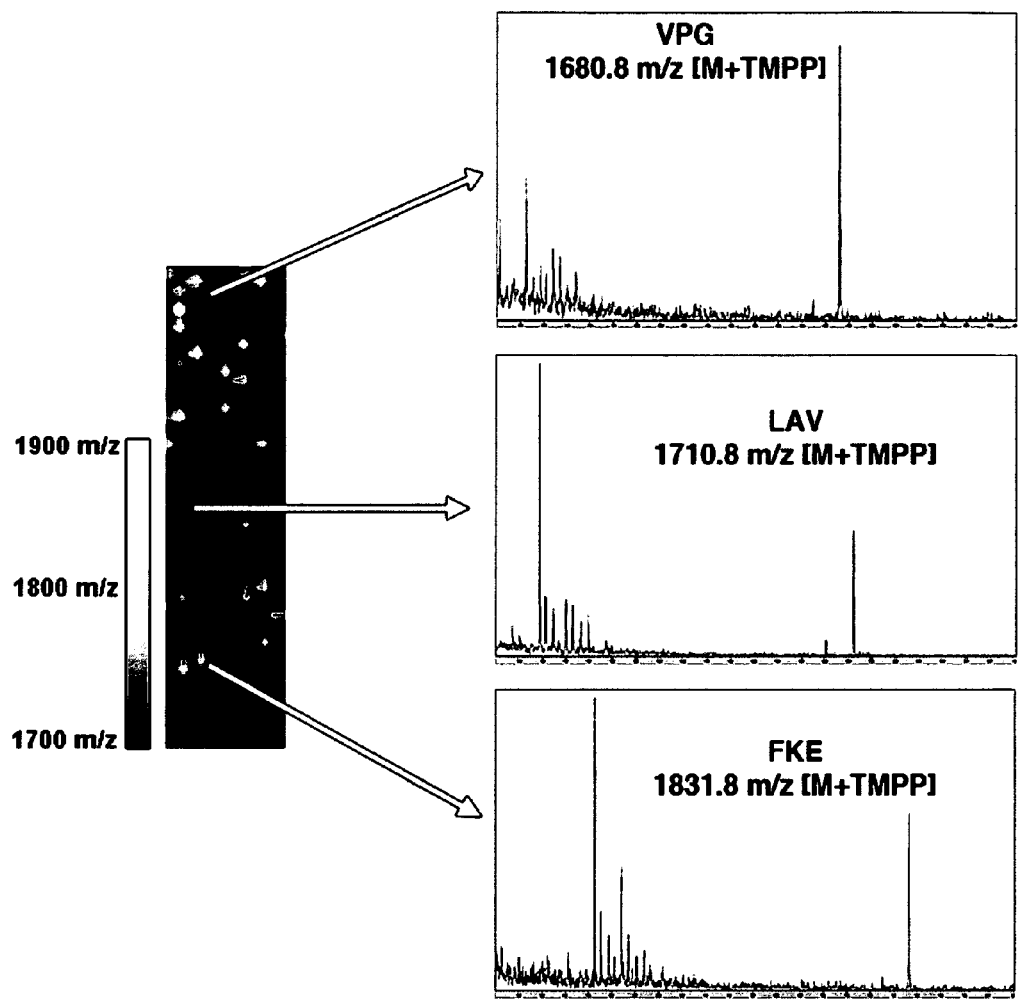
FIG. 12. Left: MALDI-TOF image of a QC region from a wafer. The features are 200 microns in size. Different peptides were synthesized in situ on each feature. The cleavable linker used was HMBA and it was cleaved by ammonia gas, an appropriate matrix was sprayed onto the surface in a way that did not cause significant diffusion and the laser associated with the MALDI TOF system was scanned in two dimensions across the surface. Right: mass spectra of peptides released from individual features.

A silicon wafer with a thermal oxide coating and a monolayer of amino silane was subjected to bulk coupling via standard amino acid coupling chemistry to Boc glycine. Quality control (QC) features 200 microns in size were generated by photodeprotection of the Boc group (generation of acid by light in photoresist followed by removal of the photoresist). HMBA was coupled to these features. A peptide was then in situ synthesized on the HMBA. The peptide was eventually released from the surface using ammonia gas which resulted in peptides not diffusing. MALDI imaging of the surface was then performed and the results are given in. FIG. 12.

Figure 13:
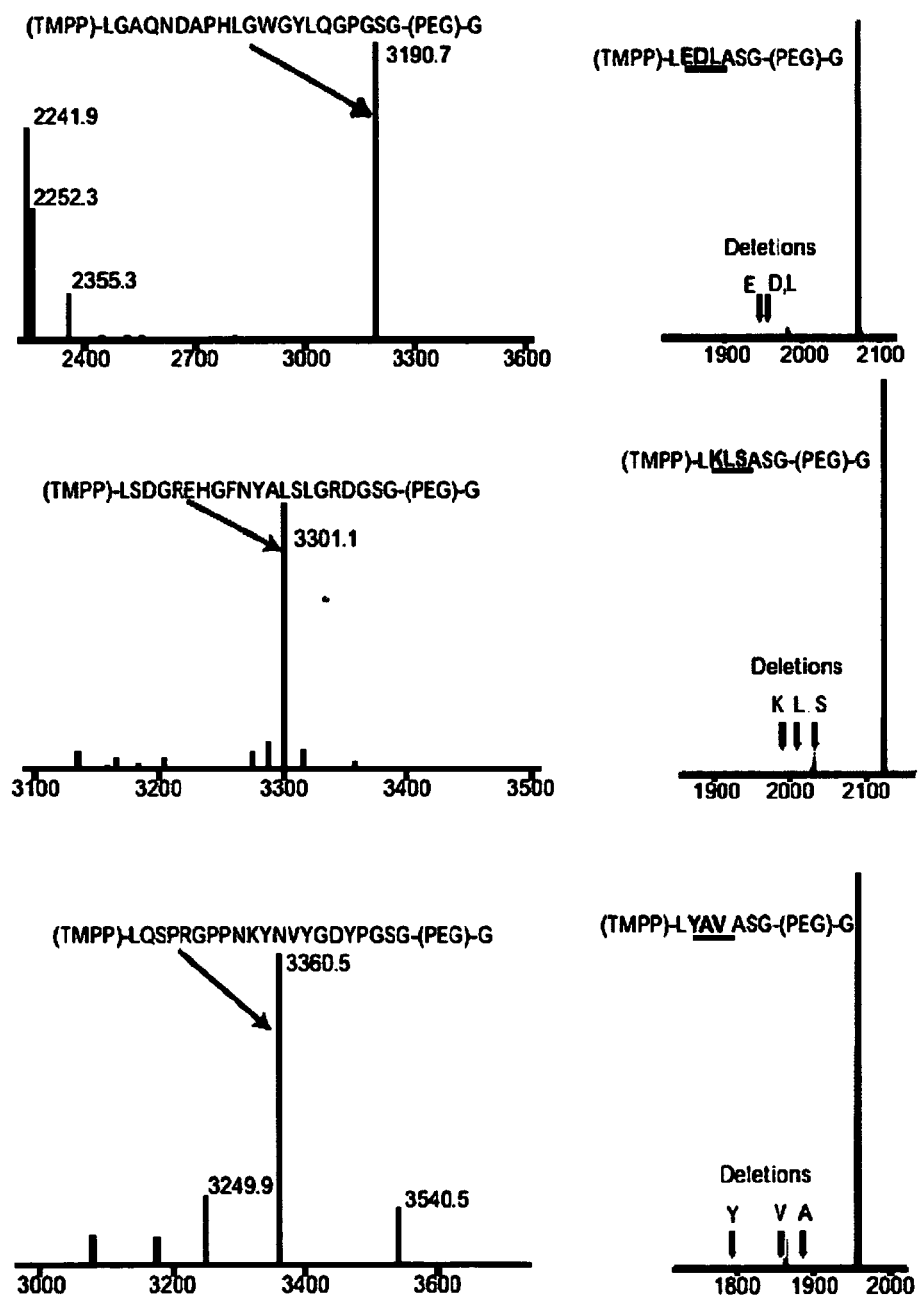
FIG. 13 is a MALDI spectra of specific QC features on the surface of an array.

MALDI-TOF analysis was used to evaluate a defined area of an array that was designated for quality control analysis. FIG. 13 illustrates the MALDI spectra of a defined area of an array comprising specific QC features. Each feature in the array analyzed in FIG. 13 was 200 microns in diameter. Plotted in the x-axis is the charge to mass ratio and plotted in the y-axis is the ion intensity of the features analyzed. In each case the dominant peaks are the expected mass to charge values for the peptides at that position in the array. The sequence of the peptide that was intended to be synthesized in the feature in question is shown for each feature. Arrows indicate positions where one might expect to find single amino acid deletions.

Example 2: Correlating Surface MALDI Measurements with Sequence Dependent Monoclonal Antibody Binding To correlate surface MALDI measurements with sequence dependent binding of monoclonal antibodies the average signals of three different monoclonal antibodies to features in a specific area of an array were measured. Binding of three select monoclonal antibodies to: a) their cognate sequences; and b) two other control sequences in a defined area of the array were measured.

Figure 14:
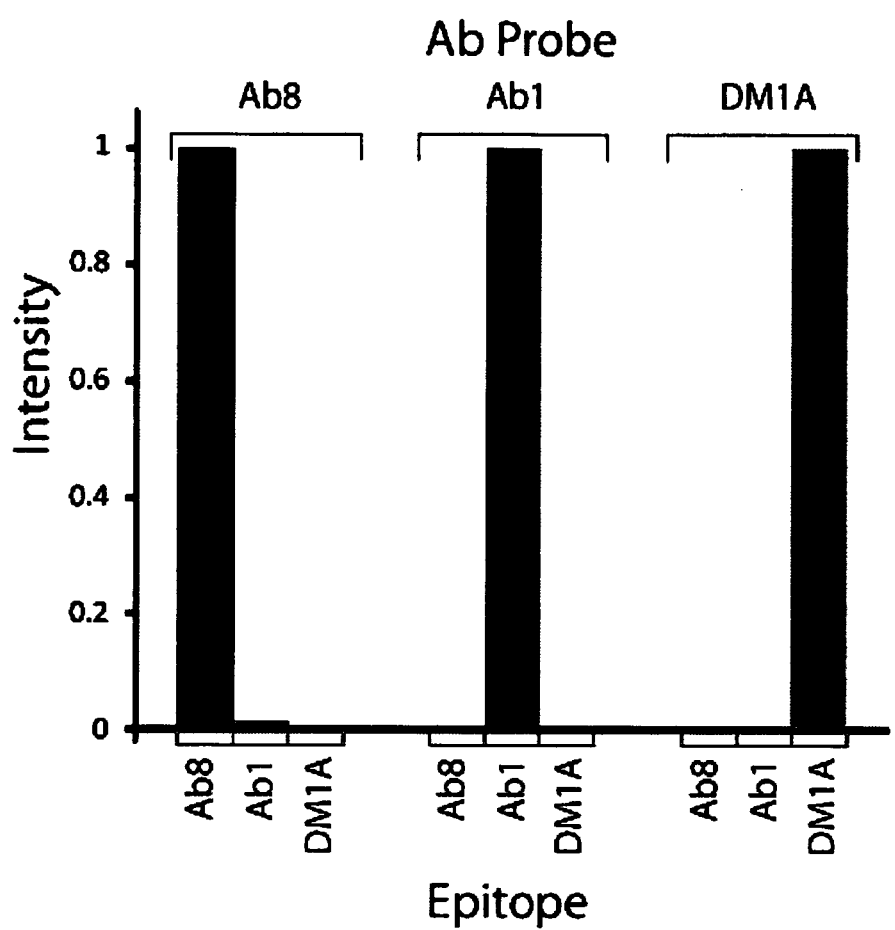
FIG. 14 is a graph correlating surface MALDI measurements with sequence dependent monoclonal antibody binding.
Figure 15:
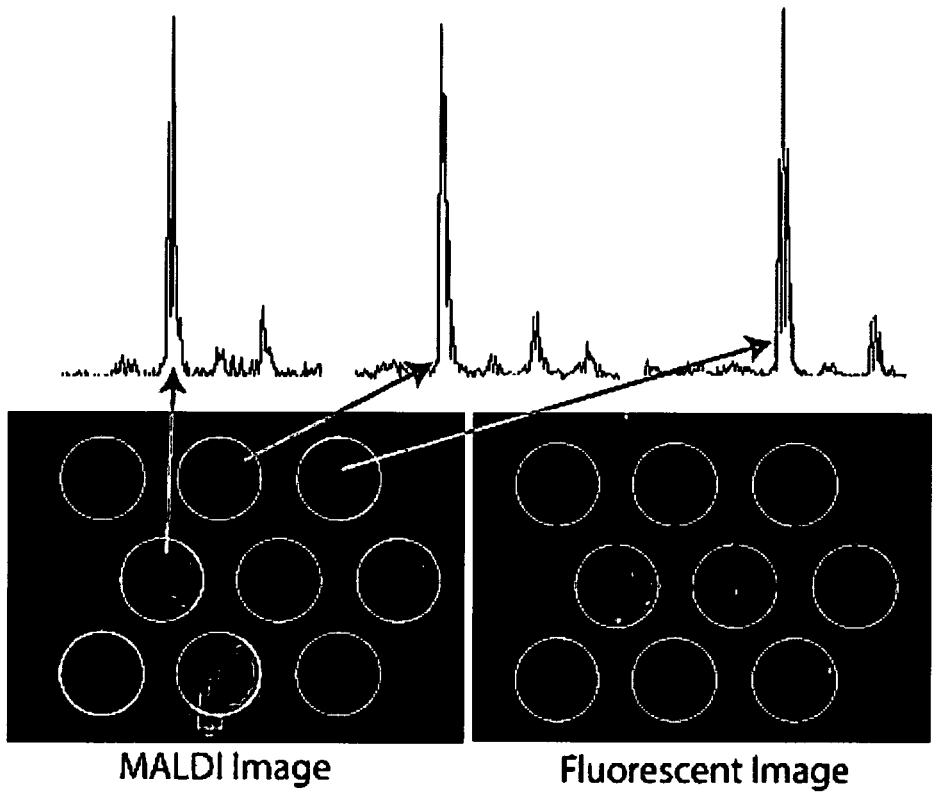
FIG. 15 illustrates the MALDI spectra of three select features shown in the Maldi image.

FIG. 14 shows the average signals associated with binding of the three different monoclonal antibodies to an array of peptides. The three monoclonals tested in this experiment were P53 Ab1, P53 Ab8 and DM1A. In each case, the detected binding level of each antibody to their respective cognate sequences was greater than 50 times the detected level of noncognate binding (FIG. 15). The actual MALDI ion counts as a function of the mass-to-charge ratio for the three select features are shown in the top of FIG. 15. The bottom left of FIG. 15 is a MALDI image of several peptide features in the defined area of the array where the specific mass signals were localized. The bottom right of FIG. 15 is a fluorescent image showing binding of the monoclonal antibody DM1A to the same defined area of the array.

The cognate sequence for the DM1A antibody is ALEKDY. The MALDI ion counts as a function of the mass-to-charge ratio for the DM1A antibody indicates that the DM1A antibody was bound to a feature comprising the known cognate epitope for DM1A. This feature comprising the ALEKDY epitope is the only features that shows substantial fluorescence, demonstrating the correspondence between antibody recognition and the ability of the surface MALDI to accurately determine the chemical species present.

Figure 16:
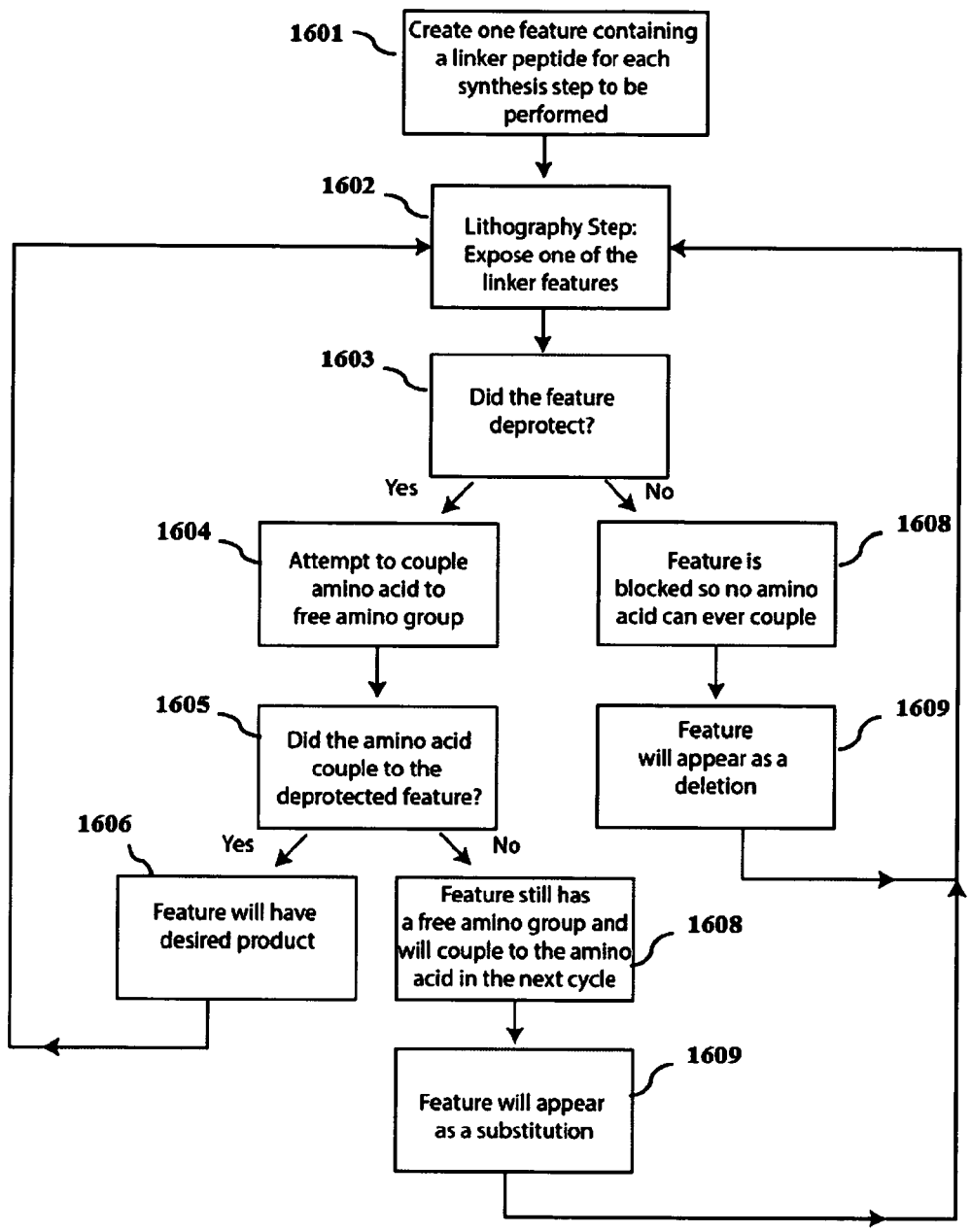
FIG. 16 illustrates a FLOWCHART for MALDI QC Analysis.

Example 3: Using MALDI Data to Monitor Photodeprotection and Coupling Steps in a Peptide Array Synthesis FIG. 16 is a flowchart summarizing steps in a process that utilizes non-covalent patterned chemical features from a defined area of an array in a MALDI-based quality control analysis of the array.

One of the first steps in the fabrication of an immunosignaturing array is to provide one or a plurality of feature(s) containing a linker peptide to the surface of the array 1601. The linker peptide can then exposed for further chemical coupling with, for example, a litography step 1602. To be available for further chemical coupling, the linker peptide needs to be exposed and deprotected in the lithography step 1603. Subsequently, additional amino acids can be coupled to the linker peptides in a step-wise fashion 1604-1605. This provides for a step-wise process whereby a desired amino acid can be incorporated into features that are present in an array. In some cases, peptides in features that are specified for quality control analysis may be cleaved from the surface by a localized or gas-phase reaction, such that the cleaved product is non-covalently associated with the surface and has not diffused outside of the original feature. These non-covalently attached features may be analyzed at the completion of the synthesis via location specific methods such as MALDI-TOF mass spectrometry.

A MALDI-based quality control analysis of the fabrication of an immunosignaturing array can determine the identity of an amino acid that is incorporated at each feature during synthesis 1606.

Figure 17:
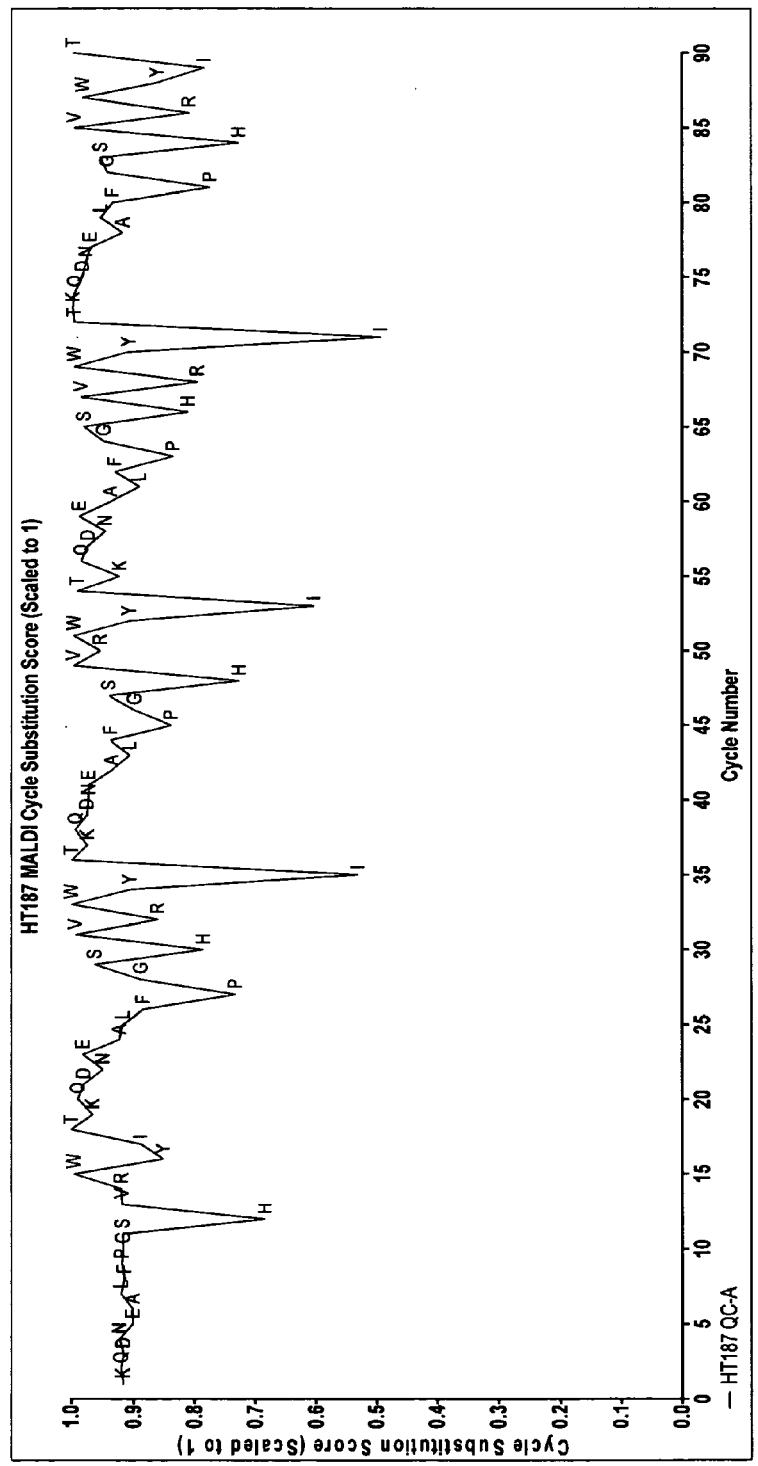
FIG. 17 illustrates a MALDI cycle substitution chart.
Figure 18:
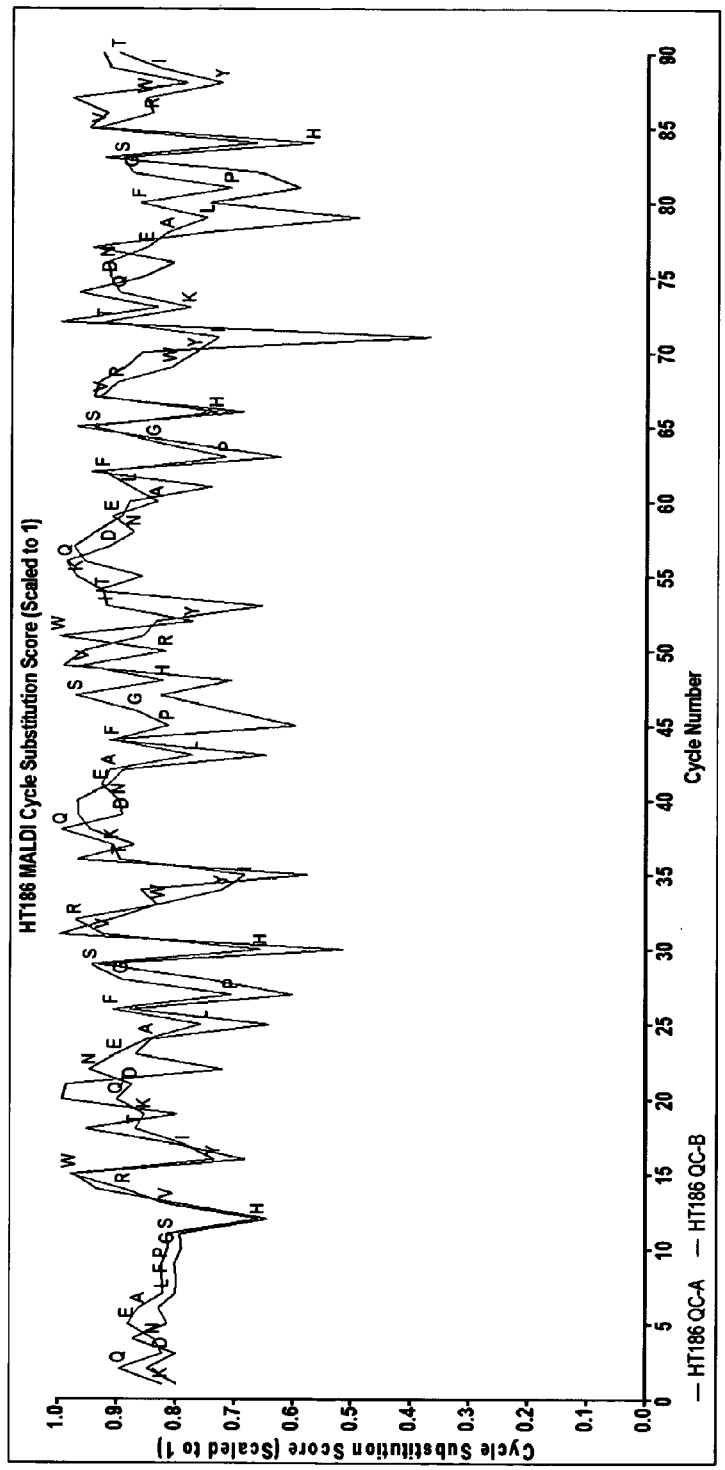
FIG. 18 illustrates a MALDI cycle substitution charts measuring variability of substitution in 2 different regions on the same wafer.
Figure 19:
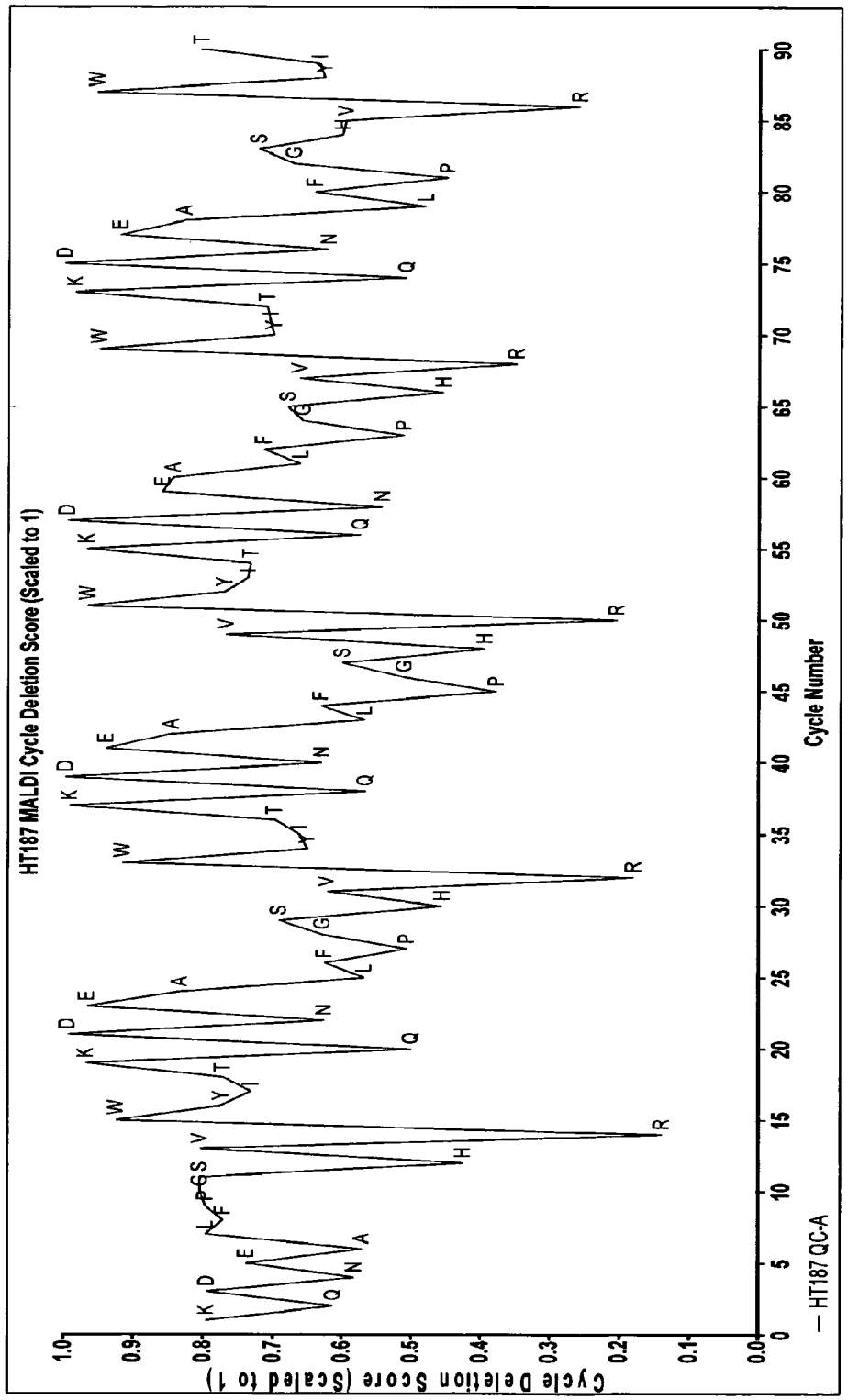
FIG. 19 illustrates a MALDI cycle deletion chart.

FIGS. 17-19 are MALDI-TOF mass spectroscopy charts that were used to monitor photodeprotection and coupling steps in the synthesis of a peptide array.

In FIG. 17 the values plotted are from a series of specific features within a defined area of the array that are designated for quality control analysis. For each feature a specific known peptide sequence was synthesized as a base or "linker" sequence. To each of these linker sequences was added a single amino acid. In this way, a feature was created for each step such that the last amino acid added was from that particular step in the process. When the coupling at a particular step was performed with no errors, the only peptide observed in the MALDI-TOF spectra was the desired peptide with the proper amino acid at the N-terminus. However, if the coupling was incomplete, some free amines would remain after the reaction and the amino acid from the subsequent coupling step would be added instead (a substitution would be observed).

The plotted values in FIG. 17 are relative coupling scores calculated from the values of the desired product in each feature compared to the value of the substitution product in each feature. Note that the scores do not represent absolute yield and must be compared to equivalent standards to calculate such yields. However results from each manufacturing lot can be compared to identify failed steps. The x-axis of the plot is the synthesis step number. Also shown for each step is the one letter code for the amino acid added at that step. In this series, there were particularly low apparent coupling values for Isoleucine couplings, suggesting that errors might have occurred in those couplings.

In FIG. 18 the values plotted are from a series of specific features within a defined area of the array that are designated for quality control analysis. For each feature a specific known peptide was synthesized as a base or "linker" sequence 1601. To each of these linker sequences was added a single amino acid. In this way, a feature was created for each step such that the last amino acid added was from that particular step in the process. When the coupling at a particular step was performed with no errors, the only peptide observed in the MALDI-TOF spectra was the desired peptide with the proper amino acid at the N-terminus (1607 and FIG. 17). However, if the coupling was incomplete, some free amines would remain after the reaction 1608 and the amino acid from the subsequent coupling step would be added instead (a substitution would be observed 1609).

The plotted values in FIG. 18 are coupling scores calculated from the values of the desired product in each feature compared to the value of the substitution product in each feature. The x-axis of the plot is the synthesis step number. Also shown for each step is the one letter code for the amino acid added at that step. The solid black line corresponds to the relative coupling score calculated for each position in one area of a particular wafer. The red solid line corresponds to a coupling score for each position in a different area of the same wafer. In this series, the average coupling score for each position (solid red line) suggests that most of the coupling steps yielded a similar signal in different places within the manufactured wafer surface. However, the relative cycle substitution score calculated for each position suggests that the coupling of the desired amino acid may have been inefficient in one region of the wafer for several of the coupling steps including might have been added to step 22 (Asparagine), step 53 (Isoleucine), step 72 (Tyrosine), and step 79 (Alanine). This could indicate, for example, that the distribution of the coupling solution was covering one region of the wafer better than the other.

This could be considered a measure of variability in two different regions of the same wafer. A measure of variability in two different regions of the same wafer can be used to determine a threshold of acceptability in quality control.

However, if the photodeprotection was incomplete, some peptides would not have their terminal amines unblocked and thus would not have been able to couple any additional amino acids 1603. This results in a deletion 1610-1611.

FIG. 19 is MALDI chart illustrating the determination of an amino acid deletion 1611. In FIG. 19 the values plotted are from a series of specific QC features generated as follows. For each feature a specific known peptide sequence was synthesized as a linker sequence. To each of these linker sequences was added a single amino acid. In this way, a feature was created for each step such that the last amino acid added was from that particular step in the process. When the photodeprotection at a particular step occurred with no errors, the only peptide observed in the MALDI spectra was the desired peptide with the proper amino acid at the N-terminus. However, if the photodeprotection was incomplete, some peptides would not have their terminal amines unblocked and thus would not have been able to couple any additional amino acids. This results in a deletion.

The plotted values in FIG. 19 are relative photodeprotection scores calculated from the values of the desired product in each feature compared to the value of the deletion product in each feature. Note that these are not absolute yields and must be compared to equivalent standards to determine yields. However, results from each manufacturing lot can be compared to identify failed steps. The x-axis of the plot is the synthesis step number. Also shown for each step is the one letter code for the amino acid added at that step.

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed in practicing the described methods. It is intended that the following claims define the scope of the embodiments and that methods and structures within the scope of these claims and their equivalents be covered thereby.

What is claimed is:

1. A method for determining the sequence fidelity of peptides synthesized on an array for quality control analysis and screening, the method comprising:
    a) assigning quality control features on a surface of the array;
    b) generating unique peptides on each control feature, each peptide having an expected sequence, wherein the peptides are synthesized in situ, and wherein the synthesized peptides on the quality control features of the array are shorter than full-length peptides synthesized on non-quality control features of the array, and wherein the synthesized peptides of the quality control features incorporate stepwise reactions corresponding to each cycle in the synthesis of the non-quality control features;
    c) releasing the peptides from the surface of the array without diffusion of the peptides outside of a boundary of the quality control features, wherein the releasing is under a volatile, nebulized or sublimated gas phase;
    d) performing matrix assisted laser desorption/ionization—time of flight analysis on the peptides released in step (c) on the array in situ;
    e) determining from a spectrum of each of the unique peptides a level of sequence fidelity relative to the expected sequence; and
    f) identifying quality control features with the spectrum less than a threshold of acceptability in quality control analysis or screening, wherein quality control features with spectrum less than a threshold of acceptability indicate failure of in situ peptide synthesis on the array.

2. The method of claim 1, wherein the array comprises a monolayer of greater than about 100 different peptides per cm$^2$.

3. The method of claim 1, wherein the array comprises a monolayer of greater than about 1,000 different peptides per cm$^2$.

4. The method of claim 1, wherein the array comprises a monolayer of greater than about 5,000 different peptides per cm$^2$.

5. The method of claim 1, wherein the peptides are not covalently bound to the surface upon generation on the array.

6. The method of claim 1, wherein the peptides are covalently bound to the surface upon generation on the array.

7. A method for determining the sequence fidelity of peptides synthesized on an array for quality control analysis and screening, the method comprising
    a) assigning quality control features on a surface of the array, wherein each quality control feature contains a linker peptide for each synthesis step to be performed;

b) initiating photolithography on one of the quality control features of step (a) containing a linker peptide;
c) performing a first fabrication cycle for a first amino acid comprising deprotection of said linker peptide followed by coupling of a first amino acid of a predetermined sequence to said linker peptide;
d) releasing the coupled amino acid from the surface of the array without diffusion but under a volatile, nebulized or sublimated gas phase;
e) querying the presence and identity of the amino acid coupled to said peptide linker using matrix-assisted laser desorption/ionization—time of flight analysis on the array in situ,
wherein if the linker peptide in step (c) was not deprotected, no amino acid would be coupled to the linker peptide and the event would be registered as a deletion of the amino acid, wherein if the amino acid in step (c) failed to couple to the linker peptide, a substitution event with a second amino acid in step (c) would be registered, and wherein the synthesized peptides on the quality control features of the array are shorter than full-length peptides synthesized on non-quality control features of the array;
f) determining a level of sequence fidelity of the quality control feature of the array relative to the predetermined sequence; and
g) identifying the quality control features with the level of sequence fidelity less than a threshold of acceptability in quality control analysis or screening, wherein quality control features with spectrum less than a threshold of acceptability indicates failure of in situ peptide synthesis on the array.

8. The method of claim 7, wherein the array comprises a monolayer of greater than about 100 peptides per $cm^2$.

9. The method of claim 7, wherein the array comprises a monolayer of greater than about 1,000 peptides per $cm^2$.

10. The method of claim 7, wherein the array comprises a monolayer of greater than about 5,000 peptides per $cm^2$.

11. The method of claim 8, wherein the linker peptides are not covalently bound to the surface upon generation on the array.

12. The method of claim 8, wherein the linker peptides are covalently bound to the surface upon generation on the array.

13. The method of claim 10, wherein the peptides to be measured are coupled to a permanently ionized group.

14. The method of claim 13, wherein the peptide is coupled to triphenylphosphine (TPP) or tris(2,4,6-trimethoxyphenyl)phosphine (TMPP).

15. A method of monitoring coupling of an amino acid to a feature on an array to in situ synthesize a peptide to determine the sequence fidelity of peptides synthesized on the array for quality control analysis and screening, the method comprising:
a) obtaining a spectra of the feature using matrix assisted laser desorption/ionization-time of flight analysis on the array in situ, wherein each feature contains a linker peptide for each synthesis step to be performed;
b) determining an identity of each amino acid incorporated for each synthesis step based on the spectra;
c) repeating steps (a) and (b) for each synthesis step to be performed; and
d) determining from the spectra a level of sequence fidelity relative to the expected sequence for quality control analysis or screening;
wherein the amino acid is releasable from the surface of the array without diffusion but under a volatile, nebulized or sublimated gas phase, wherein the synthesized peptides on a quality control feature of the array are shorter than full-length peptides synthesized on non-quality control features of the array.

16. The method of claim 15, the method further comprising calculating a cycle substitution score for each feature for each synthesis step, wherein the calculating is performed by a computer program having computer-executable code encoded therein, the computer executable code adapted to perform the calculating.

17. The method of claim 16, the method further comprising calculating an average cycle substitution score for a plurality of features for each synthesis step, wherein the calculating is performed by a computer program having computer-executable code encoded therein, the computer executable code adapted to perform the calculating.

18. The method of claim 15, the method further comprising calculating a cycle deletion score for each feature for each synthesis step, wherein the calculating is performed by a computer program having computer-executable code encoded therein, the computer executable code adapted to perform the calculating.

19. The method of claim 16, the method further comprising calculating an average cycle deletion score for a plurality of features for each synthesis step, wherein the calculating is performed by a computer program having computer-executable code encoded therein, the computer executable code adapted to perform the calculating.

20. The method of claim 16, wherein the calculated score is compared to a threshold value for a quality control determination, wherein the calculating is performed by a computer program having computer-executable code encoded therein, the computer executable code adapted to perform the calculating.

21. The method of claim 1, wherein quality control analysis includes determination of a type of error of a failed in situ synthesis, wherein the type of error is selected from a group consisting of identifying a failed synthesis cycle, a failed deprotection in a synthesis cycle, a failed coupling in a synthesis cycle, and a region of the array with one or more failed synthesis cycle.

22. The method of claim 7, wherein quality control analysis includes determination of a type of error of a failed in situ synthesis, wherein the type of error is selected from a group consisting of identifying a failed synthesis cycle, a failed deprotection in a synthesis cycle, a failed coupling in a synthesis cycle, and a region of the array with one or more failed synthesis cycle.

23. The method of claim 15, wherein quality control analysis includes determination of a type of error of a failed in situ synthesis, wherein the type of error is selected from a group consisting of identifying a failed synthesis cycle, a failed deprotection in a synthesis cycle, a failed coupling in a synthesis cycle, and a region of the array with one or more failed synthesis cycle.

* * * * *